(12) United States Patent
Witt et al.

(10) Patent No.: US 10,188,964 B2
(45) Date of Patent: Jan. 29, 2019

(54) CHROMATOGRAPHY COLUMNS

(71) Applicant: Repligen Corporation, Waltham, MA (US)

(72) Inventors: Daniel P. Witt, Charlestown, MA (US); William J. Wilde, Watertown, MA (US); Adrian Lowe, Newton, MA (US); Michael Shamashkin, Woburn, MA (US); Peter Rezac, Berlin, MA (US); Alexander Slocum, Bow, NH (US); Travis Ward, Newton, MA (US)

(73) Assignee: REPLIGEN CORPORATION, Waltham, MA (US)

(*) Notice: Subject to any disclaimer, the term of this patent is extended or adjusted under 35 U.S.C. 154(b) by 0 days.

(21) Appl. No.: 13/754,540

(22) Filed: Jan. 30, 2013

(65) Prior Publication Data
US 2013/0193052 A1 Aug. 1, 2013

Related U.S. Application Data

(60) Provisional application No. 61/592,569, filed on Jan. 30, 2012.

(51) Int. Cl.
*B01D 15/22* (2006.01)
*G01N 30/60* (2006.01)
(Continued)

(52) U.S. Cl.
CPC .......... *B01D 15/22* (2013.01); *B01D 15/206* (2013.01); *G01N 30/56* (2013.01);
(Continued)

(58) Field of Classification Search
None
See application file for complete search history.

(56) References Cited

U.S. PATENT DOCUMENTS 5,423,982 A 6/1995 Jungbauer et al.
5,693,223 A 12/1997 Yamada et al.
(Continued)

FOREIGN PATENT DOCUMENTS

EP 0655624 5/1995
EP 2239029 A1 10/2010
(Continued)

OTHER PUBLICATIONS

Chamfer. (2011). In The American Heritage dictionary of the English language. Boston, MA: Houghton Mifflin. Retrieved from http://search.credoreference.com/content/entry/hmdictenglang/chamfer/0.*

(Continued)

*Primary Examiner* — Kara M Peo

(57) ABSTRACT

A method of making and loading a chromatography column includes selecting a column tube having an appropriate elasticity, and inner diameter and length, selecting appropriately sized flow distributors, a second flow distributor having a diameter that is larger than the inner diameter of the tube, permanently securing a first flow distributor to a first end of the tube, loading packing medium into the tube, inserting the second flow distributor into a second end of the tube to drive the second flow distributor into the tube to form a sealed chamber within the tube, adjusting the longitudinal position of the second flow distributor within the tube by applying a force to the second flow distributor until it reaches a desired location within the tube, and/or forcing liquid into the chamber to move the second flow distributor and permanently securing the properly positioned second flow distributor within the tube.

17 Claims, 16 Drawing Sheets

(51) Int. Cl.
  *B01D 15/20* (2006.01)
  *G01N 30/56* (2006.01)
(52) U.S. Cl.
  CPC ..... *G01N 30/6017* (2013.01); *G01N 30/6065* (2013.01); *G01N 2030/562* (2013.01); *G01N 2030/565* (2013.01); *Y10T 29/49826* (2015.01); *Y10T 137/598* (2015.04)

(56) References Cited

U.S. PATENT DOCUMENTS

| | | | |
|---|---|---|---|
| 6,117,329 A | 9/2000 | Hargro | |
| 6,139,732 A | 10/2000 | Pelletier | |
| 6,783,673 B2* | 8/2004 | Horsman et al. | 210/198.2 |
| 6,802,968 B2* | 10/2004 | Leavesley | B01D 15/08 |
| | | | 210/198.2 |
| 7,399,410 B2* | 7/2008 | Izzo | G01N 30/603 |
| | | | 210/198.2 |
| 8,920,646 B2 | 12/2014 | Vetter et al. | |
| 2002/0153294 A1 | 10/2002 | Leavesley et al. | |
| 2003/0089662 A1 | 5/2003 | Hofmann | |
| 2007/0029241 A1 | 2/2007 | Willis et al. | |
| 2007/0114163 A1 | 5/2007 | Cummings | |
| 2009/0230060 A1* | 9/2009 | Snyder et al. | 210/656 |
| 2010/0206813 A1* | 8/2010 | Yukon | 210/656 |

FOREIGN PATENT DOCUMENTS

| | | |
|---|---|---|
| JP | H03-503212 | 7/1991 |
| JP | 2001522710 | 11/2001 |
| JP | 2001523811 | 11/2001 |
| JP | 2004505276 | 2/2004 |
| JP | 2005538376 | 12/2005 |
| WO | WO 89/07618 | 8/1989 |
| WO | WO 99/25451 | 5/1999 |
| WO | WO 2004/024285 | 3/2004 |

OTHER PUBLICATIONS

Chen et al., "Microdetermination of phosphorus," Anal. Chem., 28:1756-1758 (1956).
Gebauer et al., "Efficiency of Preparative and Process Column Distribution Systems," Journal of Chromatography, 1006:45-60 (2003).
International Search Report and Written Opinion issued in PCT/US2013/023895 dated Jun. 10, 2013 (12 pages).
Japanese Office Action in Japanese Application No. 2014-554969, dated Nov. 11, 2016, 7 pages.
Japanese Office Action in Japanese Application No. 2014-554969, dated Sep. 5, 2017, 10 pages (with English translation).
European Search Report in European Application No. 13744381.8, dated Sep. 2, 2015, 3 pages.

* cited by examiner

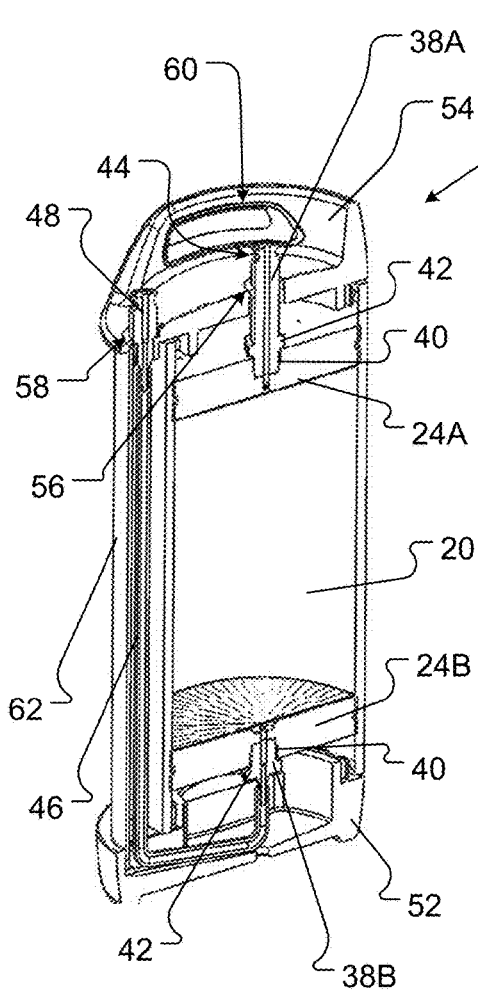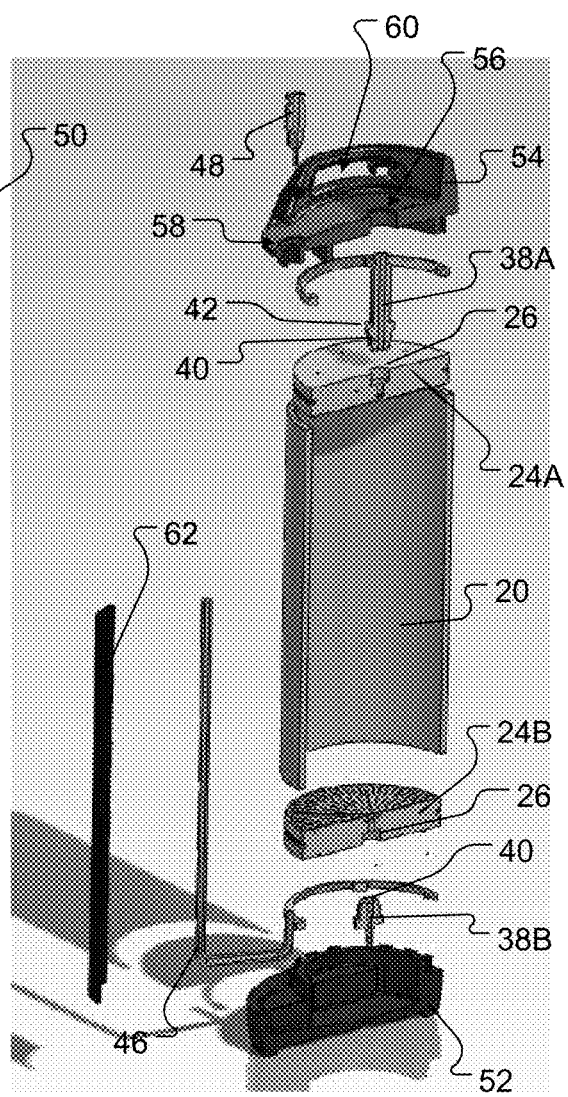
FIG. 2A
FIG. 2B

CHROMATOGRAPHY COLUMNS

CROSS REFERENCE TO RELATED APPLICATIONS

This application claims the benefit of U.S. Provisional Application No., 61/592,569, filed on Jan. 30, 2012, which is incorporated herein by reference in its entirety.

TECHNICAL FIELD

This invention relates to chromatography columns and methods of manufacture and use.

BACKGROUND

Column chromatography is a separation and/or purification technique in which a stationary "bed" of a packing medium is contained within a rigid tube. The packing medium can be in the form of particles of a solid ("stationary phase") or a solid support material coated with a liquid stationary phase. Either way, the packing medium typically fills the inside volume of the column tube.

In separation chromatography, as a liquid sample ("mobile phase") passes through the column, different compounds in the sample can associate differentially with the stationary phase such that they are slowed relative to the mobile phase and move through the column at different speeds. Thus, those compounds that associate more with the stationary phase move more slowly through the column than those that associate less, and this speed differential results in the compounds being separated from one another as they pass through and exit the column. Features of the stationary phase that promote differential association can be ionic charge (ion exchange chromatography), hydrophobicity (hydrophobic interaction chromatography), and porosity (size exclusion chromatography).

In yet another type of column chromatography, affinity chromatography, the packing medium includes binding agents, such as antigens, antibodies, or ligands, that specifically bind to one or more desired compounds or molecules in the liquid sample. Thus, as the liquid sample flows through the packing medium only the desired compounds or molecules remain in the column. A subsequent flow through the packing medium of an eluting liquid separates the desired compounds or molecules from the binding agents attached to the packing medium, or separates the binding agents from the packing medium. Either way, the desired compounds or molecules are rinsed out of the column and collected in the eluting fluid. Affinity chromatography can be used in a number of applications, including nucleic acid purification, protein purification from cell free extracts, and purification from blood.

The main components of a chromatography column are the tube, which is often made of a metal, glass, or highly rigid plastic material, and a pair of flow distributors, which are typically inserted into the two ends of the tube to form a space or chamber in the tube between the flow distributors into which the packing medium is loaded. In such columns a small space or void can form between the outer edge of the flow distributors and the inner wall of the column tube up to the point at which the O-ring is creating a seal between the flow distributors and the inner wall of the column tube. This void creates a so-called "dead zone" or "dead space" into which fluids and contaminants can enter and become entrapped and stagnant, rather than flowing through the medium within the column tube. In addition, such dead zones can become contaminated and are difficult to clean when the columns are to be reused.

SUMMARY

The invention is based, at least in part, on the discovery that if one manufactures chromatography column tubes from elastic plastic/thermoplastic and/or composite materials (such as polypropylene (PP), polyethylene (PE), polyamides, acetals, or glass-filled or carbon-filled plastics, e.g., glass-fiber and carbon-fiber plastics) and secures at least one of the two flow distributors within the column tube with a tight interference fit or press fit, the induced hoop tension opposing the interference fit between the flow distributor and the tube wall provides a sufficiently tight seal to prevent leakage and the resulting chromatography columns can be manufactured with significantly reduced dead zones around the press fit flow distributors. A second useful feature of the invention is that columns made in accordance with the description herein have an infinitely adjustable packing medium volume, also known as the medium "bed height."

In one aspect, the disclosure features methods of making and packing chromatography columns. These methods include: 1) selecting a column tube, e.g., of plastic or another appropriately elastic material, that has an appropriate inner diameter and length to accommodate a desired volume of packing medium; 2) selecting appropriately sized first and second flow distributors, wherein at least the second flow distributor (or both the first and the second flow distributors) has a diameter that is larger than the inner diameter of the tube, e.g., about 0.25 to 5.0% larger than the inner diameter of the tube; 3) permanently securing the first flow distributor to a first end of the tube; 4) adding a packing medium into the column tube; 5) inserting the second flow distributor into a second end of the tube by applying an axial force to drive the second flow distributor into the column tube to establish an interference fit, e.g., to thereby induce a hoop tension, that is sufficiently effective to from a sealed, e.g., a hydrostatically sealed, chamber within the tube between the first and second flow distributors; 6) adjusting the longitudinal position of the second flow distributor within the tube by (i) applying an additional axial force to the second flow distributor until it reaches a desired location within the column tube, or (ii) forcing liquid into the chamber to apply a hydraulic force to move the second flow distributor back towards the second end of the tube, or any combination of (i) and (ii); and 7) when the second flow distributor is properly positioned, permanently securing the second flow distributor within the tube.

The new methods can include securing both the first and second flow distributors into the tube by applying an axial force to drive the flow distributors into the tube to establish an induced hoop tension that is sufficient to produce a hydrostatic seal. This induced hoop tension, created by the interference fit between the flow distributor and the tube wall reduces or avoids the formation of any gaps between an outer circumferential surface of the first and/or second flow distributors and an inner surface of the tube. In some embodiments, the first and/or second flow distributors can be permanently secured within the tube, for example by welding or other means.

In some embodiments, the axial force to drive the second flow distributor into the tube to establish the interference fit within the tube is about 1000 lbf to about 10,000 lbf.

In some embodiments an inner surface of the tube includes a chamfer formed around at least one end of the tube to aid in inserting and centering the flow distributor into the column tube. In some of the new methods, the first flow distributor can be formed as an integral component of the tube.

In certain embodiments, wherein the packing medium can include a slurry that comprises about 40% to about 70% solids.

In another aspect, the disclosure features chromatography columns that include a plastic tube having a first end and a second end and an inner diameter $D_{Ti}$, wherein the inner diameter $D_{Ti}$ is gradually increased at the second end of the tube to an end diameter $D_{Te}$ to form a chamfer; a first flow distributor secured to a first end of the plastic tube; and a second flow distributor having an external diameter $D_{fd}$ that is greater than $D_{Ti}$ (e.g., at least 0.25%, e.g., about 0.05 to about 3.0, 1.0. 1.5, 2.0. 2.5, 3.0 or 3.5% greater); wherein the second flow distributor is secured within the second end of the tube with an interference fit directly resulting in sufficient induced hoop tension to form a hydrostatically sealed chamber within the tube between the first and second flow distributors.

In some embodiments, the plastic tube further has an increased end diameter $D_{Te}$ to form a chamfer at the first end, wherein the first flow distributor has an external diameter $D_{fd}$ that is greater than $D_{Ti}$, and wherein the first flow distributor is secured within the first end of the tube with an interference fit directly resulting in sufficient induced hoop tension. In certain embodiments, the first flow distributor is permanently bonded to the tube or both the first and second flow distributors can be secured to the inner wall of the tube with a permanent bond such as a welded joint.

In certain embodiments, the new chromatography columns can include a packing medium within the chamber. In some embodiments, the chamber is hydrostatically sealed. In certain embodiments, the chamber is constructed to withstand an internal pressure that is at least 50 pounds per square inch. In some embodiments, all three of these features are present.

In some embodiments the plastic tube and the second flow distributor are made of the same type of plastic and the first flow distributor is an integral feature of the tube.

As used herein, the term "bed height" refers to the linear height of the bed of packed chromatography media particles contained within a completed chromatography column.

As used herein, a "packed bed" refers to the final state of chromatography media particles within a chromatography column. This final state is achieved in a variety of ways. For example, one method is to combine fluid flow followed by axial compression of the bed by one or both of the flow distributors. Other methods known in the art include gravity settling of particles, vibration settling, and/or mechanical axial compression alone.

As used herein, a "flow distributor" is a component, e.g., a cylindrical component, which is secured at or near each end of a chromatography column. The flow distributors can be multi-part assemblies that serve multiple purposes. One function is to convey liquid into/out of the column by means of a port that can mate with different pipes/tubing that feed liquids into or out of the column. Another function is to direct inflow of liquid from one or multiple smaller channels to spread the liquid as evenly as possible over the entire cross-sectional area of the packed bed. Conversely the flow distributor on the outlet side of the column must efficiently gather liquid spread across the entire cross-sectional area and convey it out of the column through one or multiple smaller channels (e.g., a 200 mm column can have inlet/outlet ports of 6 mm diameter).

As used herein, a "bed support" is a net, screen, mesh, or frit that allows the passage of various liquids yet retains the small particles of packing medium that comprises the packed bed. These bed supports can be directly connected to the flow distributors.

As used herein, the terms "permanent bond" and "permanently bonded" are used to indicate that such a bond between two components cannot be separated other than by breaking the bond or one or both of the bonded components (e.g., a tube and a flow distributor).

As used herein, the term "induced hoop tension" refers to the circumferential stress generated in the wall of the tube by the insertion of a flow distributor with an outer diameter that is larger than the inner diameter of the tube. The diametrical difference between these values is referred herein as the interference fit. The induced hoop tension is triggered by internal stresses due to the interference fit as the flow distributor is forced to compress and deflect inward and the tube wall is stretched outward.

Due to the tight fit between the flow distributor and the tube wall resulting from the induced hoop tension, the new chromatography columns avoid the formation of dead zones in the vicinity of the flow distributors, which provides significant advantages in terms of flow efficiency and the ability to adequately clean the columns for reuse.

Another unique advantage of the new methods of manufacture is the ability to construct pre-packed, disposable columns with fully customizable and variable bed heights and diameters. The resolution of the specific column bed heights is limited only by the available press and linear actuator technologies used to press-fit the flow distributors through the length of column tubes. Current technologies are capable of resolving the exact location of the flow distributors within a tube to a few thousandths of an inch or better. Once a flow distributor is moved into a desired position, the induced hoop tension allows the column to withstand significant operational pressures and maintain a hydraulic seal without being permanently fixed in position. This initial seal provides the opportunity to test the performance of the column prior to permanently securing the second flow distributor. If testing reveals that column performance can be improved by an axial adjustment of the flow distributor position, such adjustment can be made and the column retested. Once the desired position has been established, the flow distributor can be permanently secured in place. To permanently secure the flow distributors in place, in some embodiments, the flow distributors can be robustly welded to the tube wall. Other methods of permanently fixing the flow distributors can be used.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2a is a schematic cross-section of the column of FIG. 1.

FIG. 2b is an exploded schematic cross-section of the column of FIG. 1.

Like reference symbols in the various drawings indicate like elements.

DETAILED DESCRIPTION

Figure 1:
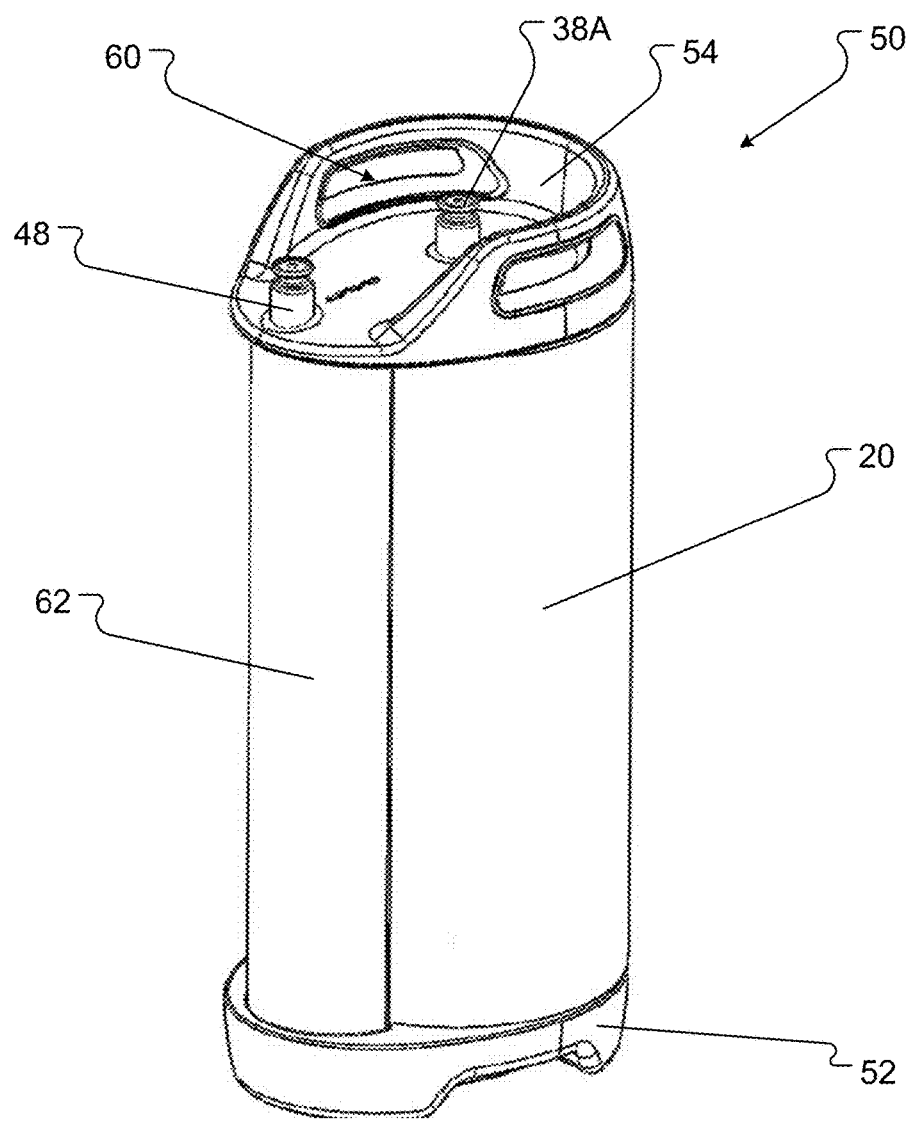
FIG. 1 is a schematic diagram of one of the chromatography columns described herein.

The new chromatography columns described herein can be made of relatively inexpensive plastic materials, and can thus be considered disposable, yet are specifically designed to be sufficiently robust to permit repeated cleaning and reuse. The new methods of manufacture described herein reduce and/or avoid the formation of dead zones around the press fit flow distributors, thus making the new chromatography columns far more effective, useful, and easier to clean than presently available chromatography columns.

Chromatography Columns

The aim of the invention is a pre-packed chromatography column for use in biopharmaceutical applications made entirely from widely available plastic/thermoplastics and/or composites (such as polypropylene (PP), polyethylene (PE), polyamides (such as various nylons), acetals, or glass-filled or carbon-filled plastics, e.g., glass-fiber and carbon-fiber plastics) or elastomeric components. The column's design is such that it can be packed with various types of chromatography packing media, or resins, to a "bed height" with infinite variability between 0 and 50 cm and longer within a given internal diameter that can be, for example, but not limited to, 10, 20, 30, 40, 50, or 60 cm or larger, up to about 80, 90, or 100 cm, or larger.

The chromatography columns described herein consist primarily of a column tube and a pair of flow distributors (or one flow distributor and one end cap). The flow distributors include a cylindrical disc and one or more inlet/outlet pipes that enable liquids to flow into and through the disc. In addition, the flow distributors can include a bed support, screen, and/or filter that are attached to the packing medium side of the flow distributor disc. The column also may or may not incorporate O-rings between the flow distributors and column tube, but the present invention can generally be used to avoid the need for O-rings entirely.

The flow path of the flow distributors can be designed according to standard practices and known designs, and the flow distributors themselves can be made, for example, of the same or a similar plastic material as the tubes, but can also be made of metal, ceramics, and other materials that are inert to the liquids and reagents that are to be flowed through the columns.

The tubes are hollow, cylindrical members, which are typically round cylinders that permit a fluid (e.g., a liquid) to flow from a first end (e.g., an upper end) to a second end (e.g., a lower end). The inner diameter of the tubes are sized and configured to receive the flow distributors for delivering fluid to and removing fluid from the tube. Based on various chromatography column performance specifications, the tubes can be made in a variety of different sizes and configurations. In some embodiments, the tubes are sized and configured to maintain structural integrity under the induced internal operating pressures of the system while being able to withstand internal pressures up to as much as about 185 psi (e.g., about 20, 30, 40, 50, or 60 psi). In some embodiments, the tubes are typically cylindrical members having an inner diameter that is about 10 cm to about 100 cm and a length that is about 10 to about 90 cm. The tubes are initially selected to be about twice as long as the desired final bed height, and are cut shorter once both flow distributors are secured in place within the column tube.

In general, the overall induced hoop tension of the tube, based on a variety of factors, can vary based on an end user's specification, such as expected internal pressure to which the chromatography column will be subjected. For example, the tube must have sufficiently thick or otherwise robust walls to avoid yielding of the tube during the insertion of the flow distributors. For example, the wall thickness of the tube can be large enough such that it can withstand adequate factors of safety above the maximum operating pressure via deriving desired induced hoop tension. For example, depending on the nature of the material, e.g., for polypropylene, a 20 cm column has a tube that has a nominal inner diameter of 199.90 mm and a nominal wall thickness of 10.0 mm. A 30 cm polypropylene column has a tube that has a nominal inner diameter of 300.00 mm and a nominal wall thickness of 13.0 mm. In some examples, depending on the nature of the material, a tube that has an inner diameter of 200 mm should have a wall thickness of from about 7.5 mm to 15 mm, e.g., about 8, 9, 10, 11, 12, or 13 mm. A tube having a diameter of 300 mm should have a wall thickness of about 10 to 20 mm, e.g., about 12, 13, 14, 15, 16, 17, or 18 mm. The wall thickness of the tube can be specified so that the tube has suitable strength to withstand internal pressure during use (e.g., about 20 psi to about 40 psi, e.g., 20, 25, 30, or 35 psi). Furthermore, adequate wall thickness helps to maintain the column geometry (e.g., volume) throughout the intended range of operating pressure, thereby limiting the amount of deflection of the column walls, which will help to ensure proper function of the columns. Walls may be thinner in tubes made from thermoplastics that are reinforced with additional structural materials such as glass or carbon fibers or particles.

In some examples, a tube should have an induced hoop tension of 25 PSI to 250 PSI, e.g., about 50, 75, 100, 125, 150, 175, 200, 225, or 250 PSI. The induced hoop tension of the tube can be specified so that the tube has suitable material properties to withstand internal pressure during use (e.g., about 20 psi to about 40 psi, e.g., 20, 25, 30, or 35 psi). Furthermore, adequate induced hoop tension helps to maintain the column geometry (e.g., volume) throughout the intended range of operating pressure, thereby limiting the amount of deflection of the column walls, which will help to ensure proper function of the claims. Adequate induced hoop tension also allows the column to withstand significant operational pressures and maintain a hydraulic seal without being permanently fixed in position.

In addition, the inner wall of the tube may be thinned or reduced in thickness at the ends, or at least at one end, to form a ramp or chamfer of from about 0.0 to about 20 degrees, e.g., about 1, 3, 5, 7, 9, 11, 13, 15, or 17 degrees, which can facilitate the insertion of the flow distributors. The chamfer should run from the end of the tube inwards from about 10 mm to about 30 mm. As discussed in detail below, the flow distributor has an outer diameter that is greater than the inner diameter of the tube, and the chamfers help align the flow distributor into the tube during manufacturing.

Figure 3A:
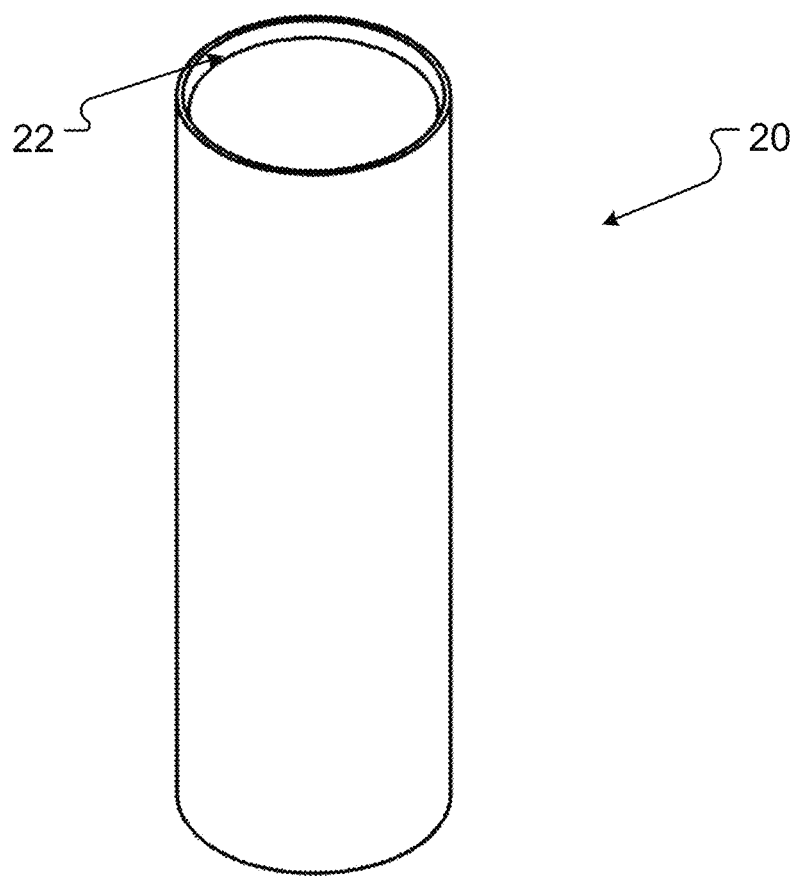
FIG. 3a is a schematic diagram of a column tube.
Figure 3B:
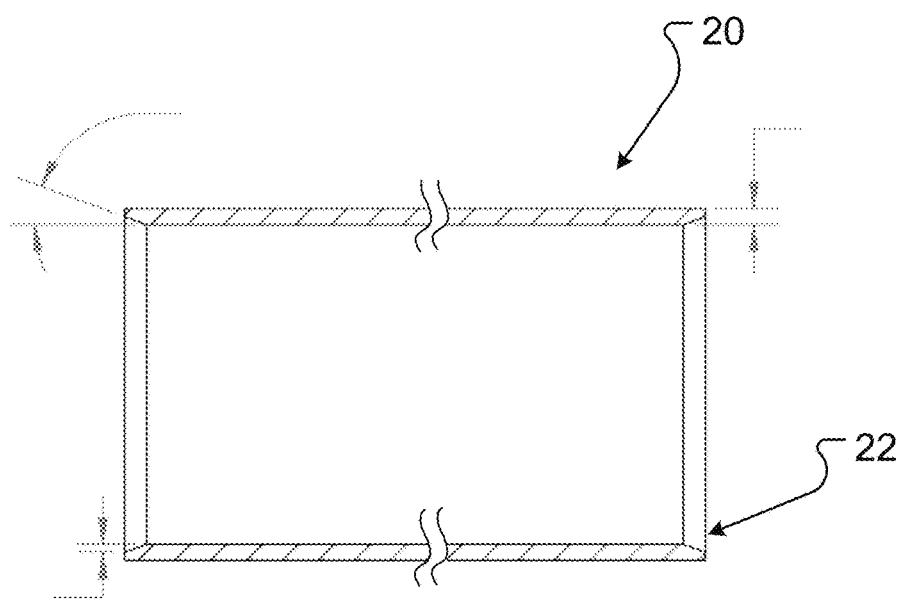
FIG. 3b is a schematic diagram of a column tube shown in cross-section.

As shown in FIGS. 3a and 3b, in some embodiments, a tube 20 is a cylinder having a chamfer 22 formed along the inner surface at each end of the tube 20. In this example, the tube 20 has a length that is about 68 cm long, an inner diameter that is about 20 cm, and a wall thickness that is about 10 mm. The chamfer 22, in this example, is about 20 degrees and runs from the end of the tube inwards about 20 mm.

Flow distributors that are sized and configured to be received in the tube 20 have an inlet hole that is hydraulically connected to an outlet hole and a network of fluid distribution conduits, such as grooves that extend from the inlet hole to the packing medium side of the flow distributor. Thus, the flow distributors are configured to receive fluid at one or more inlet locations from a first side of the flow distributor and distribute the fluid outward radially along a second side of the flow distributor that faces the packing medium when inserted into the tube. Additionally, typically by reversing the flow direction, the flow distributors can receive fluid along their entire second side and direct the fluid inward towards the one or more outlet locations on the first side.

Typically, the flow distributors are round, disc-like members that have an outer diameter that is slightly larger than the inner diameter of the tube into which they are to be inserted, such that the insertion thereof will produce an interference fit sufficient to induce a hoop tension effective to prevent leaking up to desired internal pressures. Because the flow distributor is relatively incompressible and the tube wall is relatively compliant, the interference fit causes the tube to distend leading to the formation of a liquid-tight seal. For example, for a polypropylene tube having an inner diameter of 200 mm, the polypropylene flow distributor can have an outer diameter of between 201 and 204 mm (e.g., about 202 mm). For an inner diameter of 300 mm, the outer diameter of the flow distributor can be about 302 to 306 mm. Both the tube 20 and the flow distributors 24 are designed such that the induced hoop tension during assembly is less than the yield strength of the materials. Thus, the tube walls, and in many embodiments to a lesser extent the flow distributors, experience plastic deformation and maintain their hoop tension during the life of the column. It is this hoop tension value that assures a leak-proof seal at the tube 20 and flow distributor 24 interface and limits the maximum operating pressure of the column.

The value of the hoop tension is directly related to the magnitude of the press-fit interference, the thickness of the tube wall, and the specific Young's Modulus and Poisson's Ratio of the tube 20 and flow distributor 24 materials as shown in Equation (1).

$$\sigma_{hoop\ tension} = \frac{\delta_{int}}{\frac{D_{fd}}{\varepsilon_{tube}}\left(\frac{D_{tube,o}^2 + D_{fd}^2}{D_{tube,o}^2 - D_{fd}^2} + v_{tube}\right) + \frac{D_{fd}}{\varepsilon_{fd}}(1 - v_{fd})} \quad (1)$$

where $\sigma_{hoop\ tension}$ is the induced hoop tension, $\delta_{int}$ is the interference fit (which is the difference between the outer diameter of the flow distributor and the inner diameter of the tube), $D_{fd}$ is the outer diameter of the flow distributor, $D_{tube,o}$ is the outer diameter of the tube, $\varepsilon_{tube}$ is the Young's Modulus of the tube material, $\varepsilon_{fd}$ is the Young's Modulus of the flow distributor material, $v_{tube}$ is the Poisson's Ratio for the tube material, and $v_{fd}$ is the Poisson's Ratio for the flow distributor material. Considering continuum mechanics, the induced hoop tension is simply a stress that is created in the body of the tube wall and/or flow distributor, which are only produced during the application of an external force and the subsequent deformation of the tube wall and flow distributor.

For example, in one particular implementation using polypropylene, it was found that to provide an adequate hoop tension to ensure upwards of 60 PSI operating conditions without a leak considering the available part tolerances due to various fabrication methods, a 20 cm column would need a 199.90 mm nominal inner diameter tube 20 with a 10.0 mm nominal tube wall thickness. The nominal diameter of the flow distributors 24 would need to be 202.30 mm. This would ensure at worst case interference conditions an 80 PSI induced hoop tension at each flow distributor 24. At the other end of the spectrum considering maximum interference conditions with the allowable tolerances for the tube 20 inner diameter tolerances and flow distributor 24 outer diameters, this would create up to 250 PSI induced hoop stress at each flow distributor 24.

Figure 4A:
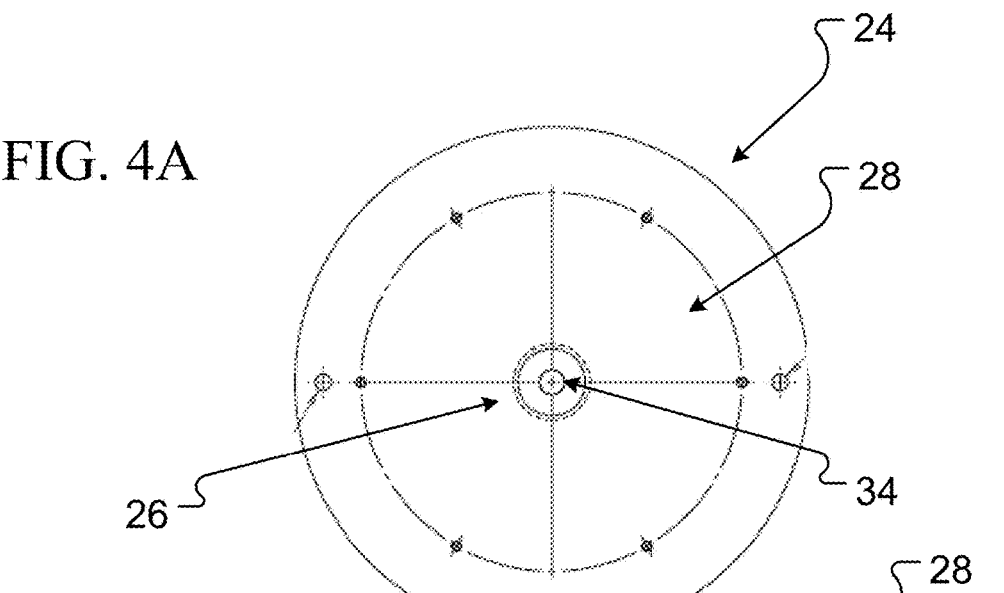
FIGS. 4a-4c are schematic diagrams of a top, front, and bottom views, respectively, of one example of a flow distributor that can be used in the new chromatography columns described herein.
Figure 4B:
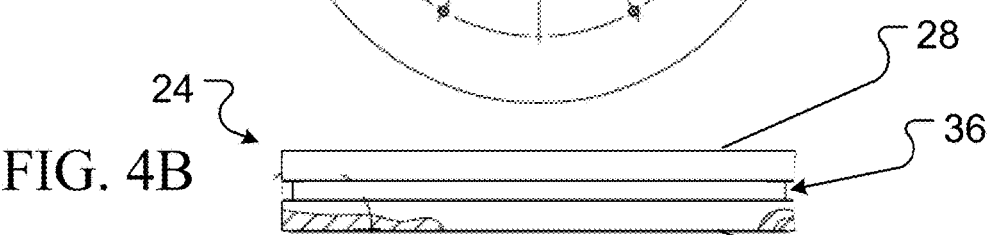
Figure 4C:
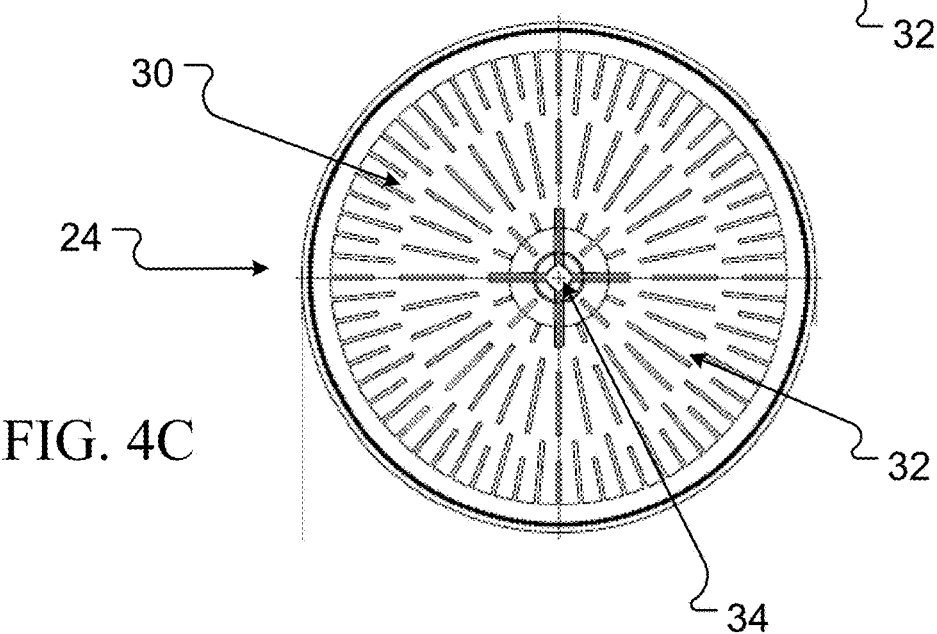

FIGS. 4a-4c illustrate that in some implementations a flow distributor 24 is a disc-like member having a fitting hole 26 formed at a central region along a first side 28 and a system of multiple grooves and channels 30 formed along a second side 32. The fitting hole 26 is a blind hole that is sized and configured to receive a fitting. The fitting hole 26 includes one or more features to receive the fitting. In one specific implementations, the fitting hole 26 is threaded to receive a threaded fitting (e.g., an M30×3.5 threaded fitting). In some embodiments, the fitting is connected to the flow distributor 24 in various other ways, such as adhesives, welding, bayonet or luer connections, or other sufficient connection techniques. In some embodiments, the fitting is manufactured as an integral component of the flow distributor 24. The flow distributor 24 also includes a fluid passage 34 to hydraulically connect the fitting hole 26 to the second side 32 of the flow distributor 24 so fluid can pass between the second side 32 of the flow distributor 24 and a fitting inserted into the fitting hole 26.

As shown, the multiple grooves and channels 30 extend substantially radially from the fluid passage 34 to direct fluid flow inward and outward radially, depending on the location of the flow distributor 24. The height or depth of the grooves is tapered from a center/feed port (e.g., the fluid passage 34) to a lower height at an outer periphery region of the flow distributor 24. An aspect ratio of this taper is the subject of various publications which provide general design guidelines (see e.g., Gebauer et al. "Efficiency of Preparative and Process Column Distribution Systems," *Journal of Chromatography* 1006 (2003) 45-60). This tapered profile can help to minimize pressure gradients radially and axially, which can negatively impact column performance (e.g., efficiency) by dispersion of target molecules travelling through the packed bed.

In some embodiments, the flow distributor 24 defines a recess 36 along its outer diameter. The recess 36 can be sized and configured to receive a sealing member (e.g., an O-ring).

The flow distributor 24 can be formed by any various manufacturing techniques, such as molding, casting, machining, or other methods, and can be obtained commercially. In some embodiments, a general shape of the flow distributor 24 is cast or molded and the grooves and channels 30 are machined from the general shape. To closely mate with the inner diameter of the tube, in some embodiments, an outer diameter of the flow distributor is formed using a lathe to ensure that the outer edge is round and to tolerance.

The fittings are mechanical attachments that can be fastened or secured to the flow distributor to deliver fluid to or remove fluid from a flow distributor and the tube in which the flow distributor is arranged. To deliver fluid, the fittings have a fluid delivery hole formed through the fitting along its central axis. The fittings also include one or more features to be received in the fitting hole of the flow distributor to retain the fitting. As shown in FIGS. 1, 2a, and 2b, in this example, fittings 38 have a threaded end 40 (e.g., an M30×3.5 threaded end) to engage the fitting hole 26. The fittings 38 also have a nut portion 42 that can be gripped by a tool (e.g., a torque wrench) for turning and securing the fitting 38 within the fitting hole 26. In some embodiments, the fitting 28 includes other types of connection mechanisms, such as adhesives, welding, bayonet or luer connections, or other sufficient connection techniques.

Fittings 38 can have different additional features based on their installed location. For example, an inlet fitting 38a that is installed on a top flow distributor 24a can have a connection feature at an end of the fitting opposite the threaded end. The connection feature, such as a hose connection, permits hose or tubing to be connected to the fitting in an easy manner. In this example, the inlet fitting 24a defines a recess 44 that is sized and configured to be received in a hose fitting, such as a sanitary fitting (e.g., a tri-clamp connection or a cam lock) style hose fitting.

Alternatively, an outlet fitting 38b that is connected to the bottom flow distributor 24b can have a different style connection than the inlet fitting. In this example the outlet fitting 38b is secured to a hose 46 to hydraulically connect the outlet fitting 38b to a remote quick disconnect outlet fitting 48. The remote quick disconnect outlet fitting 48 can be mounted or arranged in a region that can be more conveniently accessed by a user than the outlet fitting 38b.

The chromatography components described (e.g., the tube 20, the flow distributors 24a, 24b, the fittings 38a, 38b, and other components) can be made from any of various structurally and chemically suitable materials. For example, the components can be made from various plastics, such as thermoplastics (e.g., acrylonitrile butadiene styrene (ABS), acrylic (PMMA), polypropylene (PP), polyvinyl chloride (PVC), polytetrafluoroethylene (PTFE), other thermoplastics, or composites) and thermosetting plastics (e.g., epoxy resins, and fiber reinforced plastics. Material selection considerations can include the specific mechanical properties of the materials and if the materials will withstand the induced internal operating pressures of the system.

In certain specific embodiments, the tubes can be made of sufficiently elastic metals that provide an effective induced hoop tension, such as certain steels, beryllium copper alloys, titanium alloys, nickel alloys, cobalt chrome, other types of metals, or alloys of these or other metals. While metals or other materials can be used, forming the tube from plastic materials can result in producing a lower cost, and in some cases, a disposable chromatography column.

In some examples, most of the components (e.g., the tube, the flow distributors, and the fittings) are made from a thermoplastic and/or polyolefin material (e.g., such as polypropylene (PP), polyethylene (PE), polyamides, acetals, or glass-filled or carbon-filled plastics, e.g., glass-fiber and carbon-fiber plastics). Some of the components, such as the tube and flow distributors can be made from the same type of thermoplastic and can thus be welded to one another. For example, USP Class VI certified polypropylene (e.g., Product No. P9G1Z-047 from Flint Hills) or an equivalent can be used. The chromatography column components can be manufactured by any of a number of manufacturing processes known in the art, such as molding, casting, machining, composite tape laying, or other methods.

A chromatography column 50 can further include a base, e.g., a bottom end cap 52 that is sized and configured to suitably support and arrange the tube 20 and the other components in a generally vertical orientation. The base 52 includes features (e.g., holes or recesses) to receive and secure a portion (e.g., the lower portion) of the tube 20.

Foot-like protrusions extending from a lower surface of the base 52 can be included to provide a substantially level supporting surface for the chromatography column 50. The bottom end cap or base 52 can also include casters in the case of larger column diameters that cannot be easily lifted and/or carried. The base 52 is made from any various structurally suitable materials, such as metals, plastics, or composite materials. In this example, the base is made from ABS, PE, PP, or glass-filled or carbon-filled plastics, e.g., glass-fiber and carbon-fiber plastics, composite PP. In some cases, the base includes non-skid materials or features (e.g., soft rubber foot-like protrusions) to increase stability.

The chromatography column 50 can also further include a top end cap 54 that encloses the tube 20 and upper flow distributor 24a. The top cap 54 includes features (e.g., holes, recesses, or gripping elements) that receive and secure a portion (e.g., the upper portion) of the tube 20. The top cap 54 includes an inlet fitting hole 56 and an outlet fitting hole 58 that are sized and configured to receive the inlet fitting 38a and remote quick disconnect outlet fitting 48, respectively. The top cap 54 can also include one or more handles 60 that can be used to pick up and carry the chromatography column 50 or used to steer/direct larger columns that have integral casters or once placed on rolling carts/dollies. The top cap 54 is made from any various structurally suitable materials, such as metals, plastics, or composite materials that can support the weight of the chromatography column when it is lifted by the handle. In this example, the top cap is made from ABS, PE, PP, or glass-filled, e.g., glass-fiber, plastic.

A shroud or side-guard piece 62 can also be further included. The shroud piece 62 can be sized and configured to extend from the base 52 to the top cap 54 and cover some of the inner components of the chromatography column 50 (e.g., the hose 46 connecting the outlet fitting 38b to the remote outlet fitting 48). The shroud 62 can be formed of any various suitable materials such as metals, plastics, or composite materials.

Top and bottom flow distributors 24a, 24b are installed (e.g., press-fit) into the top and bottom of the tube 20 during the manufacturing and packing of the column. In some embodiments, the tube 20 and one or both of the flow distributors 24a, 24b are permanently bonded prior to insertion of the top flow distributor 24a and packing of the tube 20 with medium material. Following satisfactory testing of the column, the second, e.g., top, flow distributor 24a is permanently bonded in place.

Such permanent bonds cannot be readily separated other than by breaking the bond or the bonded items (e.g., the tube 20 and flow distributor 24a, 24b). At an upper end, an additional cap (e.g., the top cap) 54 can optionally be seated on and secured to the tube 20 and aligned so that the inlet fitting 38a installed on the flow distributor 24a at the top of the column passes through the inlet fitting hole 56 of the additional top end cap 54. Such optional top cap 54, which is primarily an aesthetic feature, can be secured to the tube 20 using various securement mechanisms, such as fasteners, adhesives, friction between the tube and the top cap, or other mechanisms.

At a lower end, the tube 20 can optionally be seated on and secured to the bottom cap (e.g., base) 52. The base 52 can be secured to the tube 20 using various securement mechanisms, such as fasteners, adhesives, friction between the tube and the bottom cap, or other mechanisms. When an optional base 52 is used, the outlet fitting 38b installed on the flow distributor 24b at the bottom of the tube 20 can extend into a cavity in the optional base 52 and the hose 46 connected to the outlet fitting 38b from the bottom flow distributor 24b is directed outward toward a region outside the periphery of the tube 20. As shown, the hose 46 can be routed out of the optional base 52 and upward along the side of the tube 20 to connect to the remote quick disconnect outlet fitting 48 that is fixed at or near the top of the column 50. By using the hose 46 and arranging the remote outlet fitting 48 near the top of the column 50, a user need not have access to the underside of the tube 20, which results in an easier to use chromatography column 50.

The tubes of the chromatography columns described herein can be packed with any solid phase medium material that is used in column chromatography as specified by the end-user. This diversity of potential packing medium materials extends to both the composition of base particles as well as their functional chemistries (e.g., affinity, ion exchange, and hydrophobic interaction). Packing medium materials can include a slurry of stationary phase particles added to an eluent solvent. Stationary phase particles can include silica gel ($SiO_2$), alumina ($Al_2O_3$), cellulose, and other suitable materials in various mesh sizes. Eluents can include one or more of various solvents, such as deionized water, ethanol or acetone.

Examples of packing media include, but are not limited to, agarose (e.g., Sepharose® Fast Flow and Capto™ from GE Health Care) controlled pore glass (ProSep® from Millipore), ceramic hydroxyapatite, polymethacrylate (e.g., ToyoPearl® media from Tosoh Bioscience), and other synthetic polymeric resins (e.g., Life Technologies' Poros™ media and Fractogel™ media from EMD).

Methods of Making Packed Chromatography Columns

One known characteristic of certain plastics/thermoplastics is their inherent compliance or ability to deform without fracturing with the application of force. The new chromatography columns are made using an assembly process that takes advantage of the "flow-ability," e.g., elasticity, of the plastics as defined by the induced hoop tension, used to make the column tube 20. The column tube 20 are made from extruded, cast, molded (injection, roto, or other), or machined plastic/thermoplastic or tape laid composite materials of specified internal and external dimensions. The designs and methods described herein for the flow distributors 24 include an outside diameter that is larger than the nominal internal diameter of the column tubes 20, described henceforth as the interference fit.

When used with cylindrical column tube 20, the flow distributors 24 must also be round, with as few (e.g., no) non-uniformities as possible on the outer surface, to ensure a uniform induced hoop tension and a sufficiently liquid-tight mating and sealing of the flow distributor 24 against the surface of the inner wall of the tube 20 when press fit into the tube 20. A sufficient degree of uniform roundness or circularity can readily be achieved by turning the flow distributor 24 on a lathe, but other methods of achieving this degree of uniform roundness are known to those skilled in the art.

The degree of acceptable interference-fit is determined by the mechanical properties, i.e., the elasticity or flow-ability, of the particular plastic/thermoplastic or composite components encompassing the tube 20 and flow distributor 24, and therefore, in the case of polypropylene, the thickness, of the tube 20 wall, but in all cases, the outer diameter of the flow distributor 24 exceeds the nominal inner diameter of the tube 20 to produce the required interference fit to assure satisfactory induced hoop tension when the flow distributor 24 is driven into the tube 20.

This assembly process provides unique advantages to the new chromatography columns. Traditional columns constructed of more dimensionally stable materials (steel, glass, etc.) are designed such that the flow distributor 24 is slightly smaller than the column tube, which is necessary to allow this component to be easily inserted and moved to the desired position within the column tube during assembly. An O-ring or similar sealing mechanism is employed around the flow distributor 24 to achieve a liquid-tight seal between the flow distributor 24 and the tube 20 wall. In these traditional designs, the combination of a flow distributor with smaller outer diameter than the tube inner diameter and the necessity to include an O-ring necessarily results in an area that is referred to as a "dead space" between the flow distributor 24 and the tube 20 wall up to the point at which the O-ring is seated. These "dead spaces" are difficult to expose to column flow and therefore pose a risk to column cleanability and resulting cleanliness. The interference fit design eliminates or greatly reduces the "dead space" of traditional columns thereby minimizing risk of carry-over contamination between column uses. The interference fit can, in some embodiments, also allow the elimination of O-rings altogether, thereby minimizing column complexity, cost, and risk to integrity due to seal failure. Another advantage of this feature is to reduce the exposure of a valuable product being purified by column chromatography to contaminants that may be released from such O-rings (typically elastomerics) that require costly and time consuming risk assessments in the form of studies of the extractables and leachables.

Figure 8:
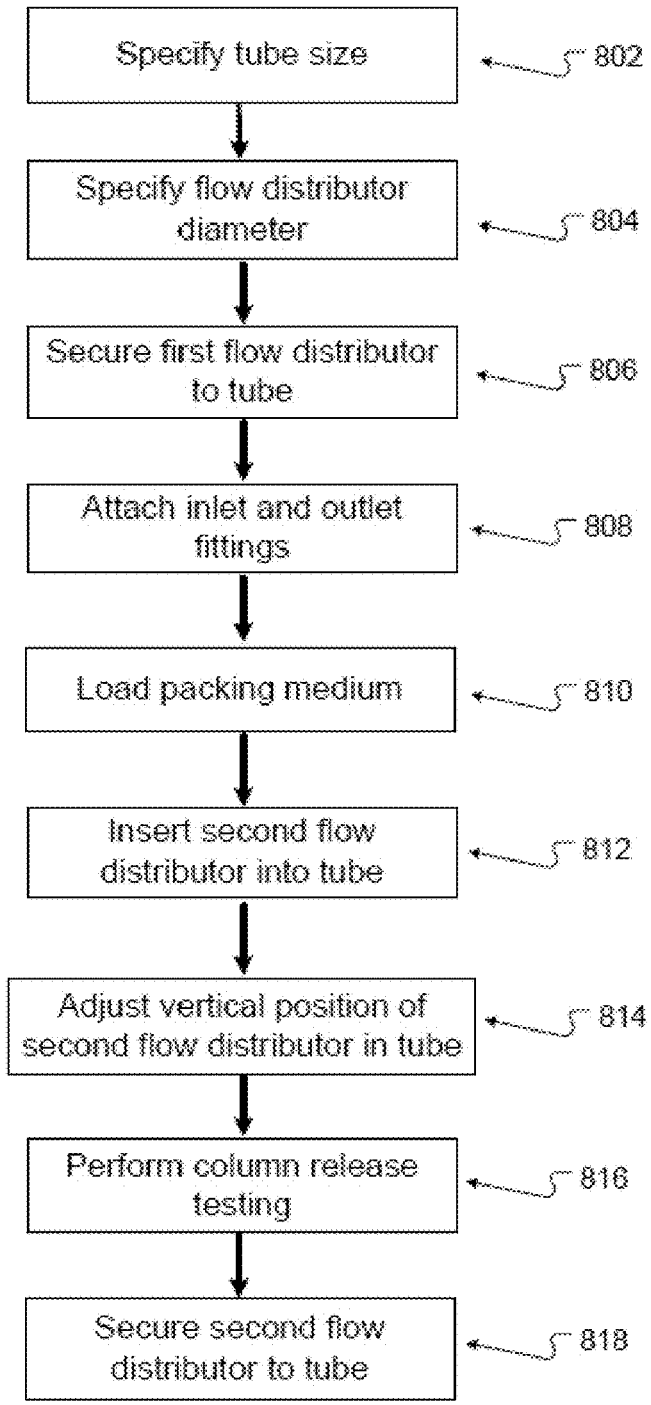
FIG. 8 is a flow chart of the basic steps in the manufacture of one of the chromatography columns described herein.

As shown in FIG. 8, the methods of making the new chromatography columns 50 include several steps.

First, specify a plastic column tube 20 that has the appropriate diameter and length to accommodate the volume of medium material that is desired for the final column (802), as well an appropriate elasticity, as described elsewhere herein. The length of the tube should be about twice the length or "bed height" of the medium material in the final column. The final length of the tube 20 can be about the same as the inner diameter, e.g., 200 and/or 199.90 mm inner diameter tube 20 might have a final length of about 150 to 250 mm, e.g., about 200 mm. The chamfer formed along the inner surface of each end of the tube is also selected. This chamfer is required to align and assist in inserting the flow distributors 24 to be driven into the interior of the column tube 20.

Second, an appropriately sized flow distributor 24 should be specified to have an outer diameter that is slightly larger, e.g., about 0.25%, 0.05 to about 3.0, 1.0. 1.5, 2.0. 2.5, 3.0 or 3.5% larger than the inner diameter ("ID") of the tube (804). For example, for a polypropylene tube having an inner diameter of and/or 199.90 mm, the flow distributor 24 should have an outer diameter ("OD") greater than 201.90 mm, e.g., of between 202 and 204, 202.5, 203, 203.5, 204, 204.5, 205, 205.5 mm). The flow distributor 24 is designed to a specific nominal OD such that it will induce sufficient hoop tension in the tube 20 wall. When selecting the appropriate nominal OD account factors to consider include the physical properties of the materials of construction (e.g., coefficient of friction, Young's modulus, modulus of elasticity, and elongation at yield) in combination with the geometries including tolerances of both the column tube's ID and its wall thickness and the tolerance of the flow distributor 240D. The forces required to press-fit the assembly together can be theoretically determined (e.g., via advanced analytical tools, such as Finite Element Analysis) and, as an alternative, this assessment may be carried out by empirical studies with specific materials of construction.

In some embodiments, the flow distributors can be made of the same material as the tube, to ensure compatibility in use and to simplify the securing of the flow distributor to the interior wall of the tube, e.g., during welding.

Figure 5:
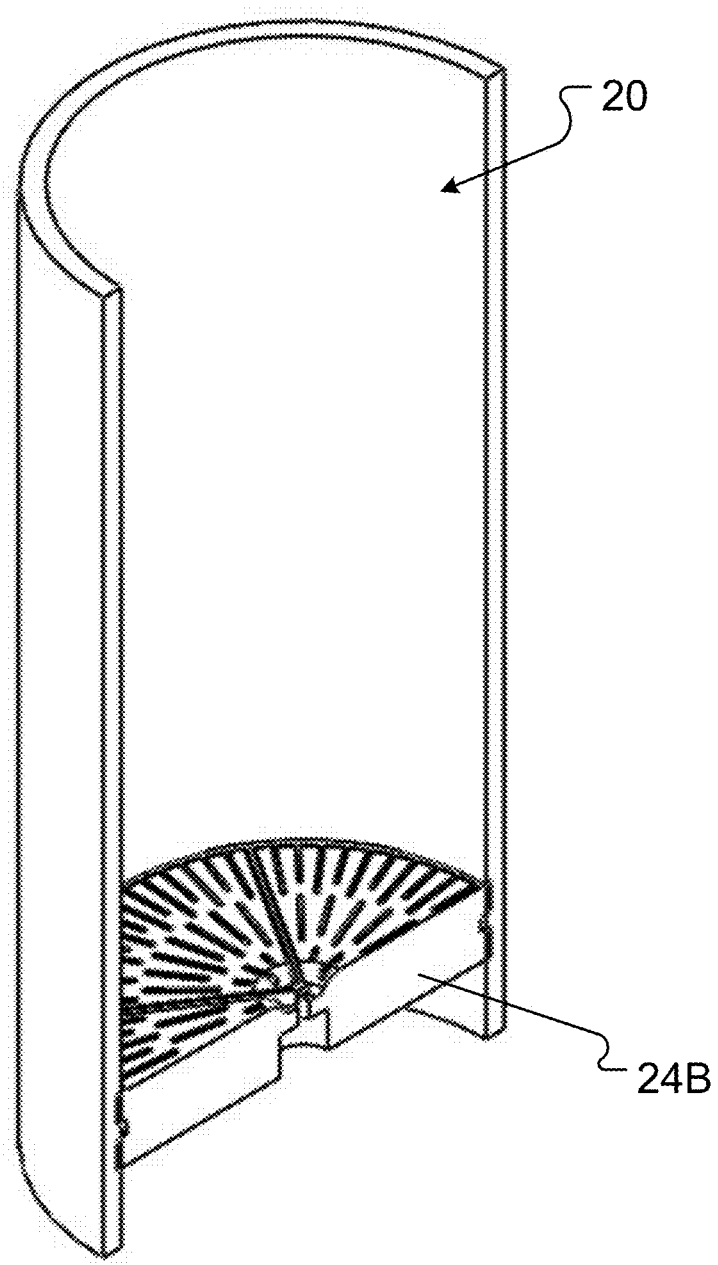
FIG. 5 is a schematic diagram of a flow distributor just after insertion into a column tube shown in cross-section.

Third, as shown in FIG. 5, a first, e.g., bottom, flow distributor 24b is secured to a first end, e.g., the bottom end, of the tube 20 (806). This can be done by any known means, or the interference fit methods described herein can be used to help avoid or reduce any dead space associated with the first flow distributor. For example, the first flow distributor 24b can be secured using metal clamps, threading cut into the tube 20 (either on the inner wall or on the outer wall) and flow distributor peripheral wall, adhesives, and various types of welding. The main point is that this first flow distributor 24b need not be moved once it is secured to the first end of the tube 20. In some embodiments, the first flow distributor 24b is formed as an integral part of the tube 20. For example, the first flow distributor can be molded as a feature of the tube 20 using known techniques.

If the interference fit method is used for the first, e.g., bottom, flow distributor, it can be initially held in place at the desired location by an induced hoop tension to provide an effective hydraulic seal at the required pressures, and then permanently secured at that location using any known means, including welding, screws, or adhesive. In particular, to establish an appropriate interference fit, the flow distributor 24 is aligned with the chamfered bottom end of the tube and then an axial force of about 1000 lbf to 10,000 lbf (e.g., 1000, 2000, 3000, 4000, 5000, 6000, 7000, 8000, 9000, or 10,000 lbf) is applied on the flow distributor 24 to drive it into the column tube 20, thereby expanding the inner diameter of the tube. For example, while the flow distributor 24 is inserted into the tube 20, both the tube 20 and the flow distributor 24 are plastically deforming to fit together, the magnitude of the tube 20 deformation is larger than the magnitude of the flow distributor 24 deformation.

The force required to drive the flow distributor into the tube depends on, amongst other factors, the angle of the chamfer formed into the tube, and other physical characteristics specific to the materials of construction (mentioned above) in combination with their geometric dimensions. For example, the axial force to drive the second flow distributor into the tube to establish the interference fit within the tube is a function of the interference fit, tube wall thickness, and specific mechanical properties of the tube and flow distributor materials. The force required to drive the flow distributor into either end of the tube can be measured by a load cell, or similar tensile testing instrument, and should be inspected during each assembly to assure adequate interference fit between the flow distributor and the tube wall. The axial force required to drive the flow distributor into the tube must be greater than and opposite to opposing forces resulting from adhesion and deformation friction forces between the tube wall and the flow distributor outer circumferential edges.

Equation 2 below describes the insertion force further.

$$F_{applied} > F_{friction,insertion} + F_{friction,deformation} = F_{friction,net} \quad (2)$$

where $F_{applied}$ is the axial force necessary to overcome the friction forces opposing the insertion of the flow distributor into the tube, $F_{friction,insertion}$ is the friction force due to adhesion between the flow distributor and tube wall materials, $F_{friction,deformation}$ is the friction force due to deformation of the flow distributor and/or tube wall, and $F_{friction,net}$ is the net frictional force. If necessary, one can differentiate the two opposing friction forces by applying a lubricant to remove the adhesion friction forces and subtracting the resulting axial force required to insert a flow distributor from the total axial force required to insert a flow distributor without the lubricant.

Alternatively, one can determine a minimum axial force to drive the flow distributor into the tube to produce a sufficient resulting induced hoop tension. This induced hoop tension acts as a radial force that holds the flow distributor at a specified location inside the tube. Considering well-known interference fit equations, an expression was derived to represent the induced hoop tension for all tube and flow distributor sizes, represented by Equation 1 above.

The induced hoop tension can be related to a total radial force exerted by the tube wall on the walls of the flow distributor by multiplying it by the circumferential area of the flow distributor in contact with the tube wall. Equation 3 below explains this further.

$$\sigma_{hoop\ tension} = \frac{F_{radial}}{A_{contact,fd}} \quad (3)$$

where $F_{radical}$ is the radial force equally distributed around the tube walls acting radially inward to the flow distributor walls and $A_{contact,fd}$ is the area of the flow distributor in contact with the tube wall. It can further be scene that this radial force is directly related to the perpendicular friction force, $F_{friction,net}$, between the flow distributor and the inner wall of the tube. Thus, one can relate the force required to overcome the friction force, $F_{applied}$, to drive the flow distributor into the tube to an induced hoop tension, $\sigma_{hoop\ tension}$, that will hold the flow distributor at a desired location inside the tube. Equations 4, 5, and 6 below describe this relationship further.

$$F_{friction,net} = F_{radial}(\mu_{friction}) \quad (4)$$

$$F_{applied} \geq F_{friction,net} = \sigma_{hoop\ tension}(A_{contact,fd})(\mu_{friction}) \quad (5)$$

and $$\sigma_{hoop\ tension} \leq \frac{F_{applied}}{(A_{contact,fd})(\mu_{friction})} \quad (6)$$

where $\mu_{friction}$ is the friction coefficient between the flow distributor material and the tube wall material.

As a result of this correlation, as long as empirical testing can assure that a given induced hoop tension will provide a leak proof seal up to adequate factors of safety above the recommended maximum operating pressure, e.g., 2×, 3×, or 4×, one can assure, and check during assembly with a load cell or similar instrument, the adequate operating pressure of the column. It is important to note that dust, humidity, oxide films, surface finish, velocity of sliding, temperature, vibration, and extent of contamination to the column and flow distributor walls can contribute to variation in the value for the coefficient of friction, $\mu_{friction}$, thus affecting the recorded insertion force. In an attempt to reduce this error, it is recommended that all initial testing to determine the accurate coefficient of friction ($\mu_{friction}$) and subsequent applied load ($F_{applied}$) to achieve the required induced hoop tension be performed in a stable, repeatable manufacturing/laboratory environment, i.e., clean room. Ultimately, it is preferred that the facility has very little dust, low humidity, minimal UV light (that could affect the mechanical properties of the materials), minimal vibrations, constant temperatures (close to room temperature conditions), low extent of contamination, and a constant insertion velocity.

In addition, the following equation was used to determine the magnitude of the surface finish on the resulting interference fit and it was shown that the surface finish (for the materials in our case) are negligible on the overall interference fit.

$$\delta_{eff} = \delta_{int} - \Delta\delta \quad (7)$$

where $\delta_{eff}$ is the effective interference and $\Delta\delta$ is the Correction to the Measured Interference considering the surface finish of the inner tube wall and the circumferential surface of the flow distributor.

$$\Delta\delta = 0.1(2)(R_{z,tube} + R_{z,fd}) \quad (8)$$

where $R_{z,tube}$ is the surface finish of the inner wall of the tube and $R_{z,fd}$ is the surface finish of the outer wall of the flow distributor.

To guarantee sufficient induced hoop stress to contain this pressure, experiments can first be carried out to develop a relationship between the amount of interference between the flow distributor and the tube wall in order to prevent leaks up to a certain pressure. Equation (1) shows that the induced hoop tension is directly responsible for creating a leak-proof seal between the flow distributor and the tube wall. Three major variables, considering constant tube and flow distributor materials, will contribute to the magnitude of the induced hoop tension: the interference fit $\delta_{int}$, outer diameter of the tube $D_{tube,o}$, and the outer diameter of the flow distributor $D_{fd}$. Once two of these values are chosen, varying the third variable will allow one to test several cases of applied force to insert the flow distributor $F_{applied}$ versus the internal pressure to leaking Once an adequate internal pressure is attained without any leaks past the flow distributors, the value of applied force can be used to back calculate the induced hoop tension necessary to contain the desired pressures. Once the necessary induced hoop tension is found for a certain chromatography column size (tube internal diameter), the three major variables that contribute to the induced hoop tension can once again be modified to optimize the design as long as they ultimately attain the same final induced hoop tension value.

Figure 9A:
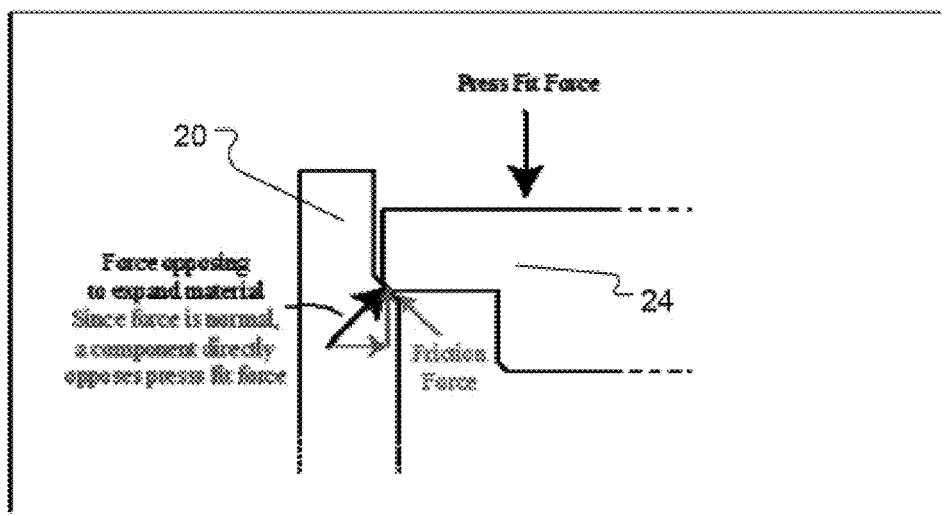
FIG. 9a is a schematic diagram of forces generated when pressing a flow distributor into a tube with a chamfered end to form an interference fit.
Figure 9B:
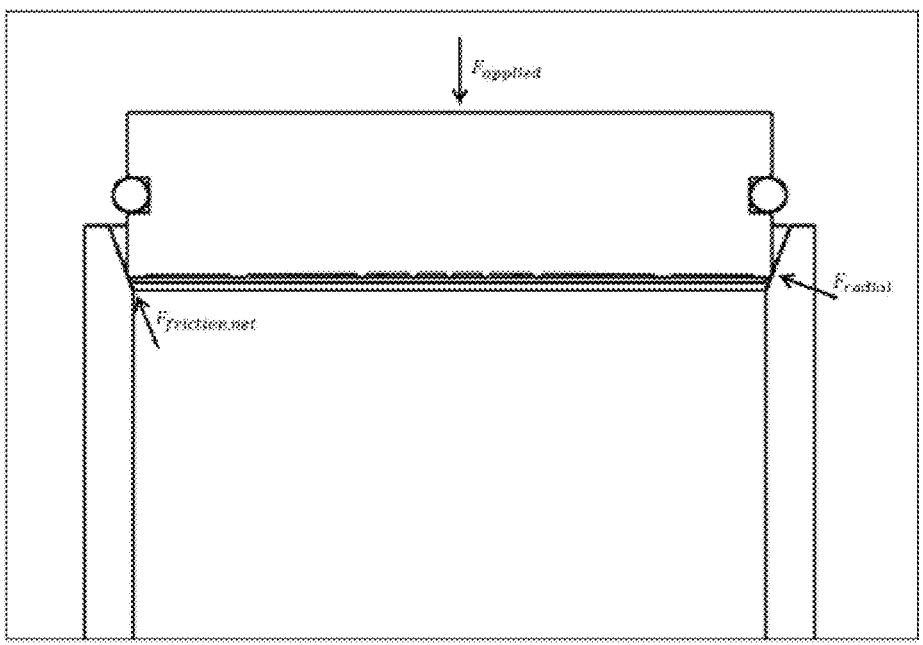
FIG. 9b is a schematic diagram of forces generated when pressing a flow distributor with an O-ring into a tube with a chamfered end to form an interference fit.

FIGS. 9a and 9b show schematic free body diagrams of the forces generated while a flow distributor 24 is initially driven into the tube 20 before it reaches a chamfer 22. As the flow distributor 24 first enters the tube 20, the tube 20 has not yet expanded. The interference between the flow distributor 24 and the tube 20 wall will force the tube 20 to enlarge and the flow distributor 24 to compress. Since the wall thickness of the tube 20 is smaller than the diameter and thickness of the flow distributor 24, the overall net force will result in expansion of the tube wall (note that the flow distributor 24 may correspondingly undergo a small amount of compression). For this to occur, the force in the axial direction must be large enough to overcome the force created due to the induced hoop tension. The axial force is from the linear actuator and the horizontal or radial force is from the induced hoop stress. The axial force is simply overcoming the frictional force. The frictional force is directly related to the value of the force from the induced hoop.

Figure 10A:
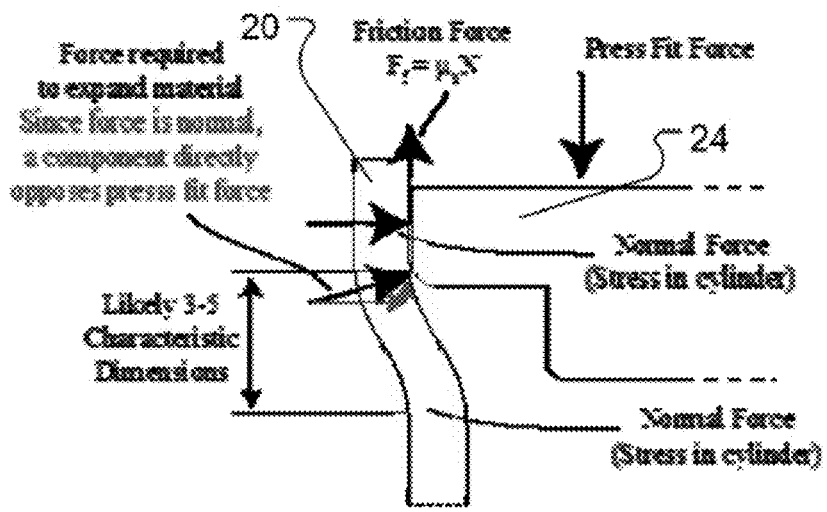
FIG. 10a is a schematic diagram of forces generated when pressing a flow distributor into a tube after an interference fit is formed.
Figure 10B:
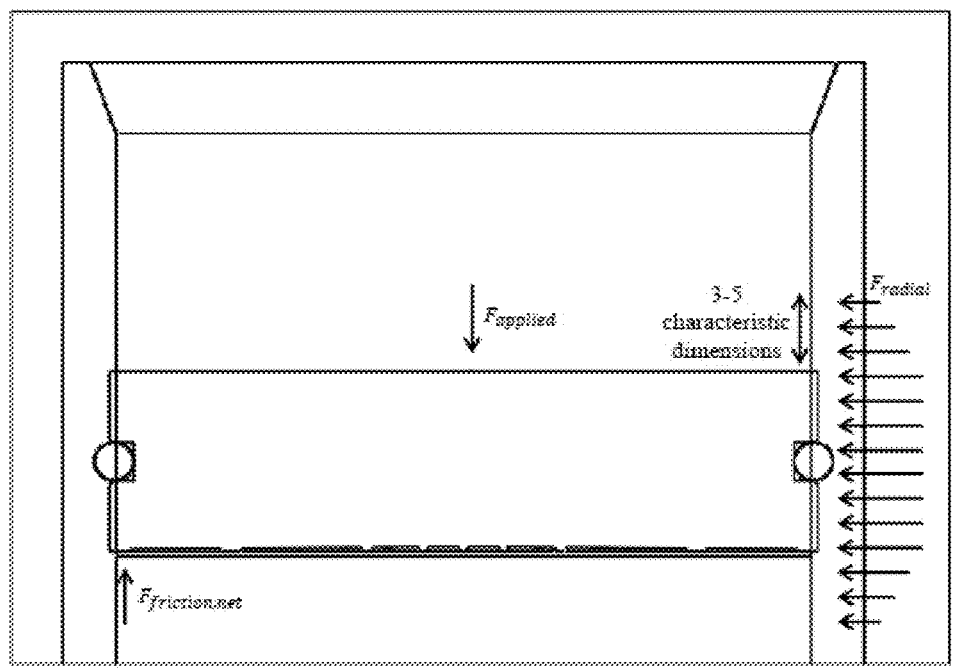
FIG. 10b is a schematic diagram of forces generated when pressing a flow distributor with an O-ring into a tube after an interference fit is formed.

FIGS. 10a and 10b show schematic, free body diagrams of the forces generated while the flow distributor 24 is driven along the axial length of the tube 20 after it passes the chamfer 22. Although some component of the axial force is contributing to expanding the tube 20, the stress is distributed 3-5 characteristic dimensions away from the initial contact point between the flow distributor 24 and the tube 20 and the tube 20 is already expanding in front of the flow distributor 24. Thus, as the flow distributor 24 is inserted axially further along the length of the tube 20, the axial force to push the flow distributor 24 is larger to overcome the higher induced hoop tension occurring not only at the point of contact with the flow distributor 24, but also 3-5 characteristic dimensions in front of the flow distributor 24. In some embodiments, the chamfer begins at the very end of the tube wall and e.g., can extend along the entire length of the tube.

Figure 11:
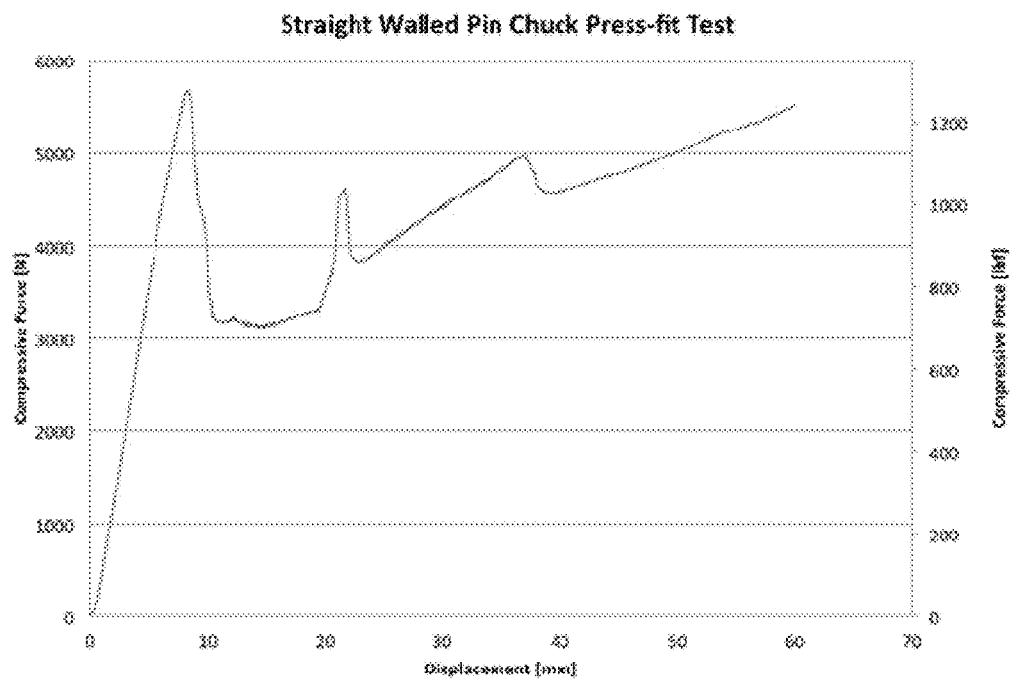
FIG. 11 is a plot illustrating an example of forces generated when pressing a flow distributor into a tube to form an interference fit.
Figure 12:
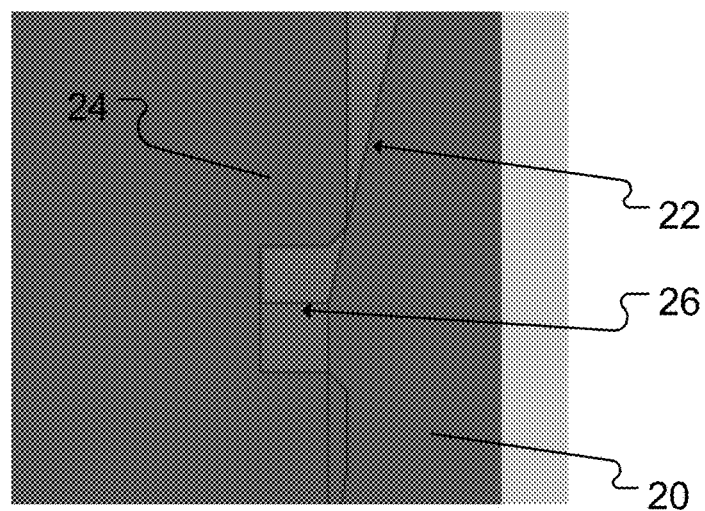
FIG. 12 is a schematic diagram of a flow distributor being driven into a tube.

FIG. 11 shows a chart illustrating the axial force required to press the flow distributor 24 into the tube 20 as the flow distributor 24 travels into the tube 20 in one embodiment. As shown, the force initially increases to a peak while a first portion of the flow distributor 24 enters and passes the beginning of the tube chamfer 22. Initially, the flow distributor 24 and tube wall are experiencing static friction and the force to overcome the static friction is greatest. Once the deformation of the flow distributor 24 and tube 20 wall give way to sliding of the flow distributor 24 into the tube 20, the force required to continue pressing the flow distributor 24 into the tube drops since it is experiencing dynamic friction. Dynamic friction is significantly less than static friction to overcome. Two additional peaks are also present in this graph. The first peak at about 21 mm corresponds to when a bottom of the chamfer 22 is in an O-ring groove 26 of the flow distributor 24 (shown in FIG. 12). The second peak corresponds to the point at which the entire flow distributor 24 is engaged in the region of the tube 20 beyond the chamfer. As shown, in this example, the maximum axial force is about 1200-1300 lbf.

For certain embodiments, the seal can be improved by the use of an O-ring arranged within an O-ring groove 26 in the outer wall of the flow distributor 24. In certain embodiments, the press-fit or interference fit is sufficient to hold the flow distributor in place, but in other embodiments, a more permanent bond is desired.

Once the flow distributor 24 has been driven about 1 to 10 cm, e.g., 6.0, 6.5, 7.0, 7.5, 8.0, or 8.5 cm, into the first, e.g., bottom, end of the tube, the flow distributor 24 can be permanently secured in place, for example by welding, e.g., if the flow distributor 24 and tube are made of the same or sufficiently similar materials. Various welding techniques can be employed to form the weld between flow distributor and column tube including, but not limited to, hot tool welding, hot gas welding (e.g., at 420° C.), ultrasonic, extrusion, laser, conductive, high frequency, etc. If the two pieces are made of different materials, they can be connected using mechanical clamps, such as metal hose clamps, applied externally to compress the tube and apply a force that will anchor the flow distributor within the tube at that location, or by adhesives or by mechanical fasteners that pass through the tube wall and into the flow distributor.

Fourth, the inlet and outlet fittings 38a, 38b are attached to the first (e.g., bottom) and second (e.g., top) flow distributors 24a, 24b (808). The inlet and outlet fittings 38a, 38b have threaded regions 40 that are screwed into threaded fitting holes 26 in top and bottom flow distributors 24a, 24b. A recess (e.g., an O-ring gland) can be formed either at a bottom end of the each fitting (i.e., an end that mates with a flow distributor) or in a terminal end of the threaded fitting hole 26 of the flow distributor. In this example, an O-ring is arranged between the fittings 38 and the flow distributors 24 to form a seal (e.g., a liquid-tight seal) between the fittings 38 and the flow distributors when they are threaded together. A torque wrench can be used to ensure adequate compression of the O-ring to create sufficient seal at this interface.

Fifth, the packing medium in the form of a liquid slurry is loaded into the column tube 20 in the space (chamber) above the bottom flow distributor 24b (810).

Figure 6:
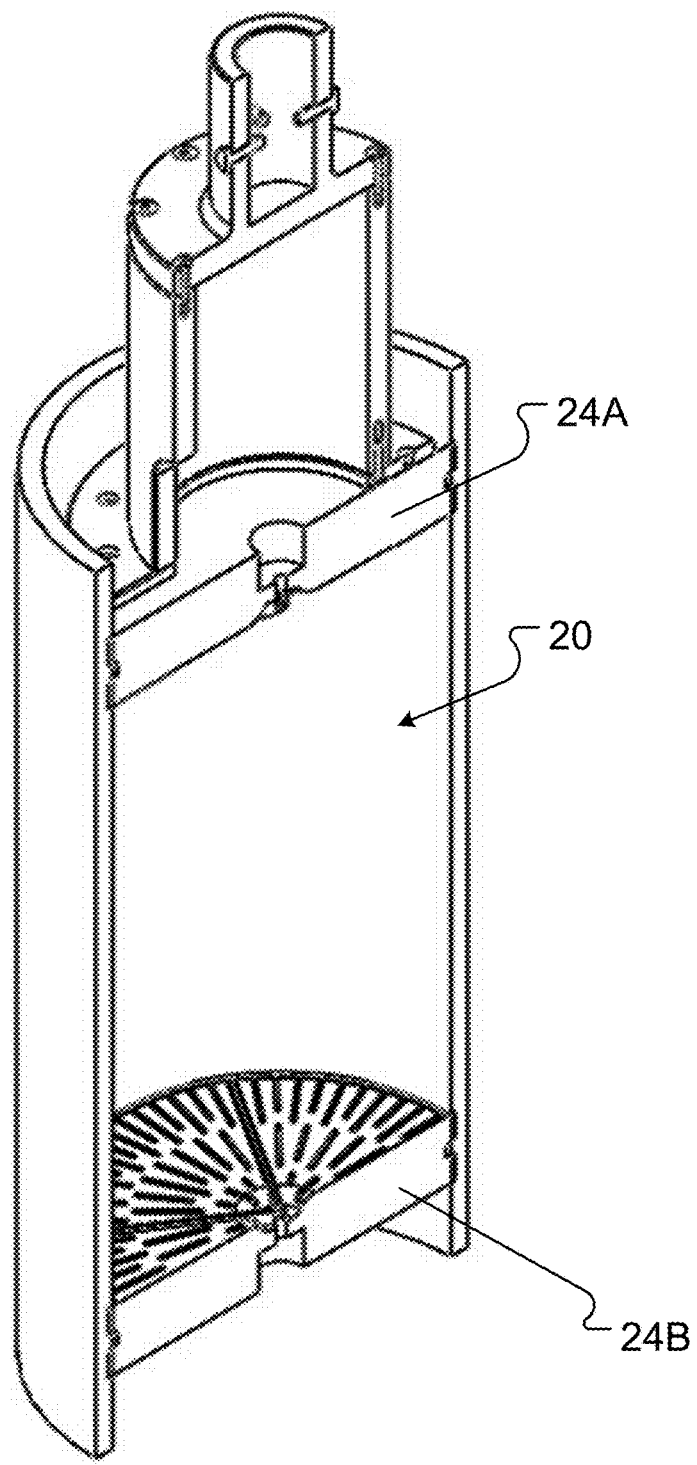
FIG. 6 is a schematic diagram of a column tube within a press used to apply axial force to a top flow distributor to drive it into the column tube to provide a tight interference fit shown in cross-section.
Figure 7:
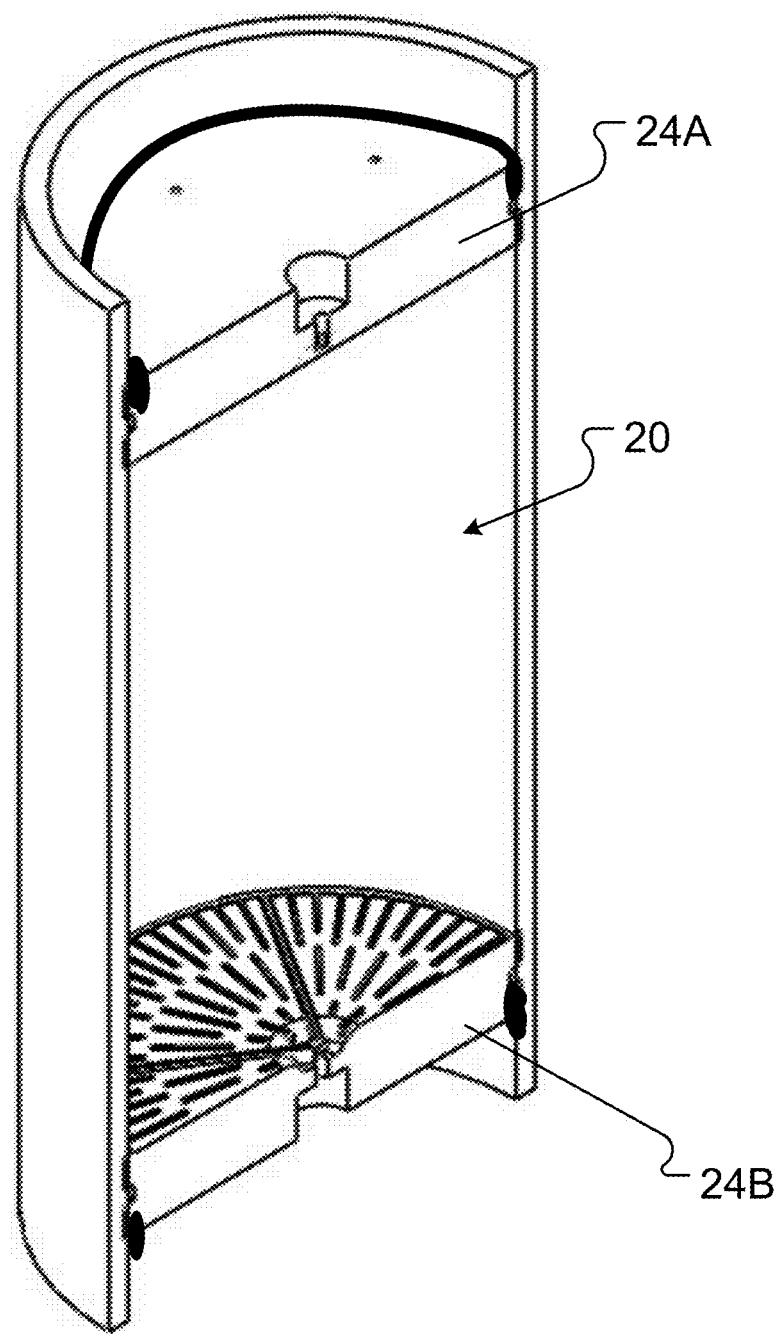
FIG. 7 is a schematic diagram of a chromatography column after the top flow distributor has been welded in place.

Sixth, as shown in FIGS. 6 and 7, once the second, e.g., top, flow distributor 24a is plumbed with tubing (and optionally already connected to a liquid source) it is inserted into the tube 20 in much the same way as the first flow distributor 24b is inserted when using the interference fit method (812). It is important that the interference fit method is used for the second flow distributor, because the initial location to which this second (e.g., top) flow distributor 24a is driven into the tube 20 should not be immediately fixed, because it may be desirable to readjust the initial position of the second flow distributor following testing. Thus, the interference fit method is used, so that the second, e.g., top, flow distributor 24a can be moved internally within the tube 20 to make final adjustments. It is also important that the interference fit be designed and implemented such that it ensures a liquid-tight seal at the pressures used during testing of the column.

At this point, the packing medium can be actively settled into a packed bed using a method suitable for the particular medium, for example, flow with an appropriately formulated solution ("mobile phase" or "packing buffer") or suction applied from the column outlet fitting 38b, or any other suitable known techniques or methods. The second, e.g., top, flow distributor can be driven further into the tube by applying an additional axial force to the flow distributor until it contacts the packing medium and may compress the packing medium to reach a desired position. Such compression can range from none at all to 30% or more of the packed bed height depending on the nature of the packing medium. The performance of the column as measured by HETP (Height Equivalent to a Theoretical Plate) testing and asymmetry analysis will be a function, in part, of the compression of the bed. If appropriate, it is also possible to move the inserted flow distributor 24a out towards the end of the tube to reduce bed compression. This is done using hydrostatic pressure by applying a force to the liquid inside the chamber created between the first and second flow distributors. Since the first flow distributor 24B is permanently secured, the second flow distributor 24A, which is secured using a press fit, will move once a force sufficient to overcome the press fit is exerted against it by the liquid within the column tube.

Seventh, suitability of the column packing medium can be tested by a pulse injection of an unretained and readily detectible test article (e.g., acetone via UV monitoring or sodium chloride via conductivity monitoring) (818). Based on the outcome of the packing test, the top flow distributor 24a can travel down (e.g., can be driven) further into the packed bed and the packing test can be repeated. If the top flow distributor is moved too far into the tube, which can result in over compressing the packed bed, liquid can be forced into the chamber through the inlet fitting with the outlet fitting sealed shut thereby using hydraulic force to move the top flow distributor 24a back towards the top end of the tube and reducing compression of the packed bed. Once suitability of column packing is determined, the column can then be sanitized and/or flushed with a bacteriostatic storage solution per end-user specifications.

Eighth, when the second, e.g., top, flow distributor 24a is properly positioned, it can be permanently secured, such as by welding or other means as noted above for securing the first flow distributor (818). In some embodiments, the interference fit may suffice to secure the top (or second) flow distributor 24a to the inner wall of the tube 20.

In some embodiments, the loaded final chromatography column can then be fitted with a top cap, a base, and/or a side guard. The chromatography column can then undergo final sterilization and be used or packaged for shipping.

Testing of Packed Columns

Evaluation of packed columns can include an HETP (Height Equivalent to a Theoretical Plate) test and asymmetry analysis. The HETP/asymmetry tests measure the quality of the packed bed using injection of a small volume of a readily detectable chemical test article (e.g., acetone, NaCl) that does not interact with the column resin. In a well-packed bed, the test article will move through the column uniformly and will elute as a narrow symmetrical peak. The results are expressed as plates per meter (N/m).

The number of plates (N) in a column is given by:

$$N = 5.54 \times \left(\frac{V_e}{W_h}\right)^2 \quad (9)$$

where $W_h$ is the peak width at half height of a retention volume peak response curve and $V_e$ is the retention volume.

Plates per meter (N/m) is calculated as:

$$\frac{N}{m} = \left(\frac{N}{L(m)}\right) \quad (10)$$

where L(m) is the packed bed height expressed in meters.

$$HETP = \frac{L}{N} \quad (11)$$

where L is the packed bed height and N is the number of theoretical plates as calculated above.

Asymmetry ($A_s$) is defined as b/a, where "a" is a horizontal distance from a point at 10% of the leading edge of a retention volume peak response curve to a vertical center line at the peak, and "b" is a horizontal distance from the vertical center line to a point at 10% of the trailing edge of the retention volume peak response curve.

For additional, general details regarding chromatography, please refer to *Handbook of Process Chromatography, 2nd Ed.*, by Hagel, Jagschies, and Sofer, which is hereby incorporated by reference.

Methods of Use

The systems and methods described herein provide end-users with disposable, pre-packed, and pre-qualified chromatography columns that are comparable in performance to other chromatography columns that typically exist in a durable hardware installation requiring significant capital expenditure. The column tube's construction of polymeric materials enables it to be manufactured quickly, easily, and less expensively while maintaining robust form and function and simple operation for up to 10-20 or more usage cycles. The new columns are used in the same manner as other known chromatography columns, but given the disposability, the new columns are especially useful for separating and purifying reagents that are toxic or otherwise hazardous, e.g., viruses, pathogens, and explosives.

However, the new chromatography columns are surprisingly robust and can be used repeatedly. In addition, the design of the new chromatography columns provides easy cleaning for such reuse, and the new chromatography columns will provide at least 5 to 10 cycles of use.

EXAMPLES

The invention is further described in the following examples, which do not limit the scope of the invention described in the claims.

Example 1—Pressure Testing of Press-Fit Seals and Welded Seals

The purpose of this example is to pressure test press-fit assemblies of extruded polypropylene (PP) column tubes and machined PP end pieces (e.g., to simulate flow distributors) without O-rings. After testing the sealing ability of the press-fit, the columns were welded on both ends and re-pressurized to challenge the strength of the hot-gas welding attachment method.

Materials 200 mm (nominal) ID PP column tubes (ID and OD machined)

Figure 13:
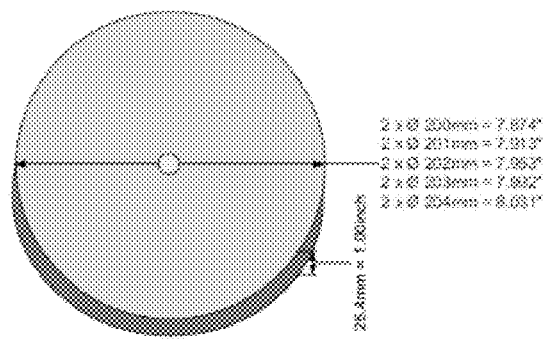
FIG. 13 is a schematic diagram of an end piece used during pressure testing.

2 each of 200 mm, 201 mm, 202 mm, 203 mm, 204 mm PP end pieces per FIG. 13. The end pieces are sized and configured to resemble structural characteristics of flow distributors.

Exlar linear actuator (GSX50), Repligen ECN Number: E0376

Harbor Freight 20 ton hydraulic press

Leister hot gas welder 5 mm×3 mm triangular shaped welding rod

200 PSI hydraulic pressure test assembly

Methods

All machined column tubes were measured at 8 points to obtain a minimum, maximum, and average inner diameter.

The first ("lower") end pieces were press-fit into column tubes using an Exlar linear actuator (Exlar, Minnesota).

For all column assemblies the lower press fit pieces were hot gas welded in place, filled with water, and second ("upper") end piece was press-fit into column tubes again using the Exlar linear actuator.

The column tube upper end was restrained with the hydraulic press and hydrostatic pressure was incrementally increased until water was visibly observed to bypass the press-fit seal.

Following breach of press-fit seal, the assemblies were de-pressurized and "upper" end piece was hot gas welded in place Welded pressure assemblies were again subjected to hydrostatic pressure testing to assess effectiveness of weld to perform hydraulic sealing as well as mechanical strength.

Results

Table 2 summarizes the data obtained from this series of experiments. During pressurization, the internal pressure was measured while the tube to end piece joint area was visibly observed for leaks.

TABLE 1

| End OD | Tube ID | Interference (diametric, mm) | Leak Pressure (psi) | Welded Pressure Hold (psi) |
|---|---|---|---|---|
| 200 | 199.5 | 0.5 | 15 | 65+ |
| 201 | 199.5 | 1.5 | 45 | 165 |
| 202 | 199.5 | 2.5 | 74 | 175+ |
| 203 | 199.5 | 3.5 | 85 | 140+ |
| 204 | 200 | 4 | 100 | 190+ |

+Welds were still integral at these pressure points.

Hydraulic sealing of the press-fit increased linearly between 0.5 mm and 2.5 mm of diametric interference, with each additional millimeter imparting approximately 30 psi (~2 Bar) improvement in sealing ability. Increasing interference from 2.5 mm to 3.5 mm increased sealing ability by approximately 11 psi (~0.76 Bar). FIG. 14 is a plot of leak pressure based on the amount of diametric interference and graphically represents the observed sealing trend.

Figure 15:
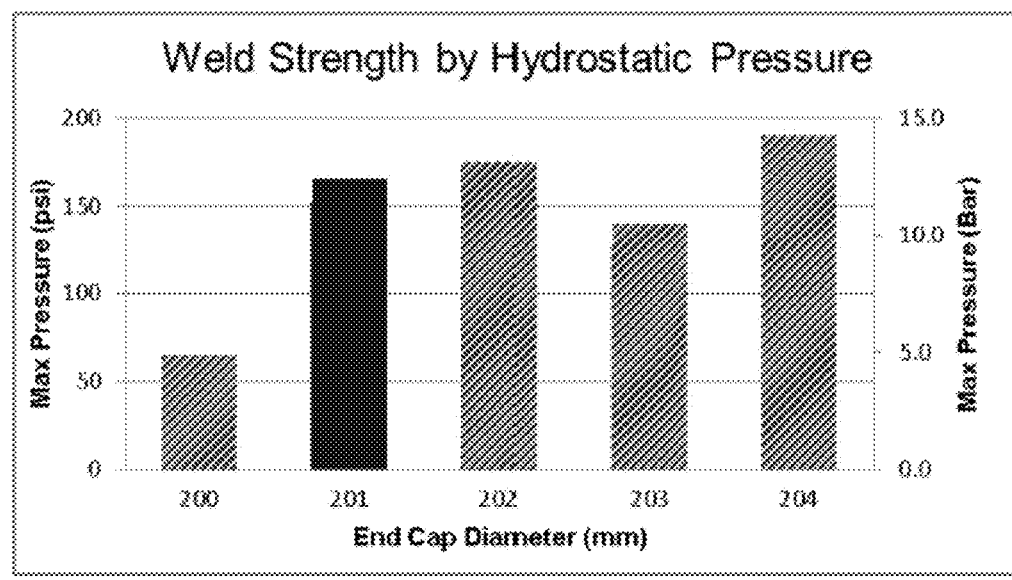
FIG. 15 is a plot illustrating weld strength performance for different press-fit configurations of a tube and an end piece.

Table 2 also summarizes the data obtained when fully welded (i.e., top and bottom end pieces welded in place) press-fit assemblies were re-pressurized to challenge weld strength. A portion of weld in the column tube with the 201 mm end pieces did yield at 165 psi (11.4 Bar). The welds of the other assemblies could not be tested to failure. Excessive leaking past weld gaps and/or threaded inputs/outputs did not allow pressurization beyond the points reported in table 1. Furthermore, in all columns but the test subject with an end cap diameter of 202 mm, the welds did not prevent weld seams from leaking at/around the leak pressures observed prior to welding. FIG. 15 graphically represents the observed weld strengths of the four assemblies.

FIG. 15 is plot of observed weld strength based on various degrees of interference. The test subject with an end cap diameter of 201 mm was the only assembly yielded to pressure. Excessive leaking past weld gaps and/or threaded inputs/outputs in other assemblies did not allow further pressurization.

Conclusion

Based upon the data collected in this study, press-fitting alone can achieve a leak pressure (hydrostatic sealing pressure) of 85 psi (5.9 Bar) at 3.5 mm of diametric interference distance and even 100 psi at 4.0 mm of diametric interference distance, which are both more than sufficient to provide an initial attachment of a flow distributor that is effective for column testing under normal operating conditions. Weld strength tests (welded pressure hold) show that seals over 165 psi can be achieved and support this approach as a viable method to permanently secure the flow distributors to the inner wall surface of the column tubes to provide a significant safety factor well above normal operating pressures that might arise during use of these columns.

Example 2—Pressure Testing of Induced Hoop Tension and Welded Pucks (Flow Distributors)

The purpose of this example is to assemble pucks (solid cylindrical discs with outer dimensions similar to flow distributors), with a range of outer diameters, with tubes. The pucks were machined from blocks of polypropylene (PP) and fitted with ports to permit the introduction of liquid. All of the tubes were PP manufactured by extrusion to a nominal inner diameter and wall thickness. These tests were conducted with pucks that did not contain O-rings or O-ring grooves in an effort to attain an accurate induced hoop tension value for each interference fit. Pucks were axially forced into tubes (two pucks per tube, one at each end) and each column was pressurized with water and observed for leaks. After testing the sealing ability of the interference fit, the pucks were welded to the tubes on both ends and re-pressurized to challenge the strength of the hot-gas welding attachment method.

Materials
  199.90 mm (nominal) ID PP tubes with 10.0 mm nominal wall thickness
  (2) nos. of each puck size, each 25.4 mm thick per FIG. 13
    200.0 mm nominal diameter
    201.0 mm nominal diameter
    202.0 mm nominal diameter
    203.0 mm nominal diameter
    204.0 mm nominal diameter
  Exlar linear actuator (GSX50)
  Harbor Freight 20 ton hydraulic press
  Leister hot gas welder
  5 mm×3 mm triangular shaped PP welding rod
  200 PSI hydraulic pressure test assembly
Methods All PP tubes were measured at 8 points to obtain a minimum, maximum, and average inner diameter along the axial length of the tube.

One puck was axially forced into one end of a tube using the Exlar linear actuator. This first puck was hot gas welded in place for all assemblies. The columns were filled with water, and then a second end piece (with identical nominal outer diameter) was forced into the opposite end of the tube using the Exlar linear actuator. The hydraulic press was then lined up with the second puck, which had not been welded in place to assure that the puck did not experience any axial movement while the column was pressurized. The hydraulic press helped to minimize sources of leaking and assure that leaking was a direct result of overcoming the induced hoop tension between the puck and the tube wall.

After leaking was observed, the columns were depressurized and the second puck was welded in place. Finally the column was pressurized a second time to check the new pressure at which leaking was observed. During all pressure testing, the internal pressure was ramped up from ambient pressures by 5 PSI increments and allowed to stabilize at each new pressure for 30 seconds before checking for leaks and increasing the internal pressure again if no leaks were detected.

Results

Figure 14A:
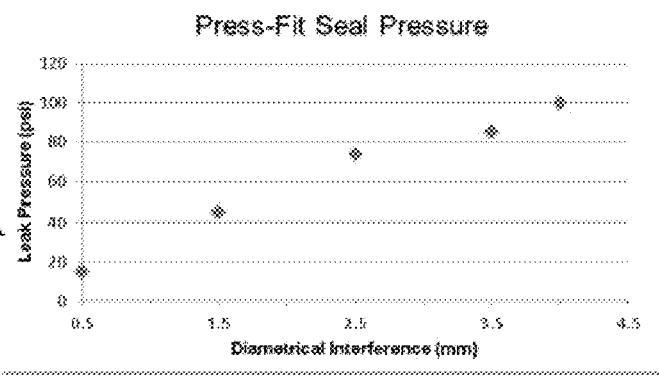
FIG. 14a is a plot illustrating press-fit seal performance for different press-fit configurations of a tube and an end piece.
Figure 14B:
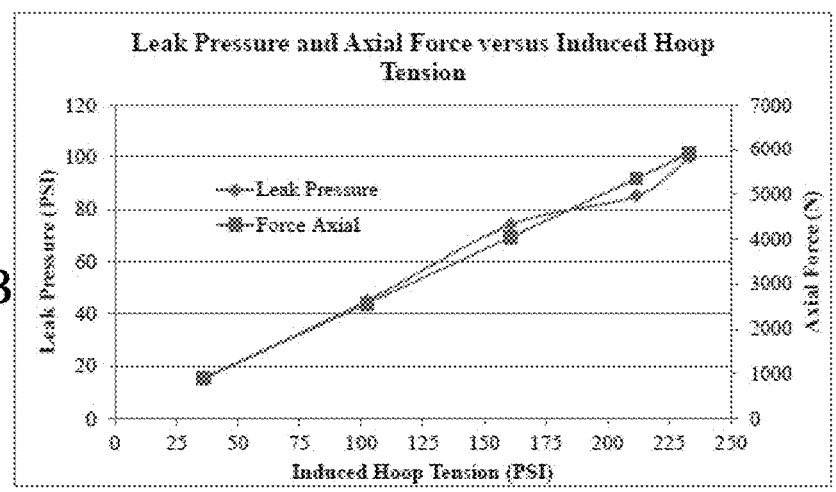
FIG. 14b is a plot illustrating the Leak Pressure and Axial Force required to insert a flow distributor into the tube versus the Induced Hoop Tension.

Table 3 along with FIGS. 14a, 14b, and 15 summarizes the data obtained from this series of experiments. During pressurization, the internal pressure was measured while the tube to end piece joint area was visibly observed for leaks.

TABLE 2

| End OD | Tube ID | Interference (diametric, mm) | Leak Pressure (psi) | Welded Pressure Hold (psi) |
|---|---|---|---|---|
| 200 | 199.5 | 0.5 | 15 | 65+ |
| 201 | 199.5 | 1.5 | 45 | 165 |
| 202 | 199.5 | 2.5 | 74 | 175+ |
| 203 | 199.5 | 3.5 | 85 | 140+ |
| 204 | 200 | 4 | 100 | 190+ |

+Welds were still integral at these pressure points.

Hydraulic sealing of the press-fit increased linearly between 0.5 mm and 2.5 mm of diametric interference, with each additional millimeter imparting approximately 30 psi (~2 Bar) improvement in sealing ability. Increasing interference from 2.5 mm to 3.5 mm increased sealing ability by approximately 11 psi (~0.76 Bar). FIG. 14a is a plot of leak pressure based on the amount of diametric interference and graphically represents the observed sealing trend while FIG. 14b describes the induced hoop tension (PSI) versus the observed leak pressure and required applied axial load to insert the puck. This aspect of the experiment is important in determining operating conditions. For example, this work illustrated that to attain an operating pressure of up to 85 PSI, one would need to design the 20 cm column to contain an induced hoop tension greater or equal to 150 PSI.

To assure that this value of induced hoop tension has been attained, FIG. 14b shows that during assembly, one would want to see an axial load greater or equal to 5350 N to insert the puck into the tube. It is important to note from Equation 4 that the radial force exerted as a result of the induced hoop tension is linearly related to the applied force that is required to force the puck into the tube by the coefficient of friction. For the two materials used in this work, an initial experiment was carried out to determine an accurate coefficient of friction between these materials as 0.23. Exploring this further, a range of columns can be built with varying tube wall thickness, tube inner diameter, and puck (flow distributor) outer diameters while the considering material properties as long as the induced hoop tension and, as a direct result, the axial force to insert the puck (flow distributor) is greater than a known value Table 3 also summarizes the data obtained when fully welded (i.e., top and bottom pucks both welded to the tube wall) press-fit assemblies were re-pressurized to challenge weld strength. A portion of weld in the column tube with the 201 mm end pieces did yield at 165 psi (11.4 Bar). The welds of the other assemblies could not be tested to failure. Excessive leaking past weld gaps and/or threaded inputs/outputs did not allow pressurization beyond the points reported in table 1. Furthermore, in all columns but the test subject with an end cap diameter of 202 mm, the welds did not prevent weld seams from leaking at/around the leak pressures observed prior to welding. FIG. 15 graphically represents the observed weld strengths of the four assemblies.

FIG. 15 is a plot of observed weld strength based on various magnitudes of interference. The test subject with an end cap diameter of 201 mm was the only assembly that yielded to pressure. Excessive leaking past weld gaps and/or threaded inputs/outputs in other assemblies did not allow further pressurization.

Conclusion

Based upon the data collected in this study, the induced hoop tension created by an interference fit alone can achieve a leak pressure (hydrostatic sealing pressure) of 85 PSI (5.9 Bar) at 3.5 mm of diametric interference and upwards of 100 PSI at 4.0 mm of diametric interference, which are both more than sufficient to provide an initial attachment of a flow distributor that is effective for column testing under normal operating conditions. Weld strength tests (welded pressure hold) show that seals over 165 PSI can be achieved and support this approach as a viable method to permanently secure the flow distributors to the inner wall surface of the column tubes to provide a significant safety factor well above normal operating pressures that might arise during use of these columns.

Example 3—Testing of Column Tube Packing Medium

A column tube was packed using a commercially available packing medium material based on synthetic polymer (e.g., polymethacrylate) particles functionalized to have hydrophobic interaction (HIC) properties. The axial forces required to achieve a suitable degree of induced hoop tension as a result of the magnitude of the interference fit between the column tube and flow distributors were recorded and plotted. Column packing evaluation tests are in-line with functional requirements of this particular media type.

Materials
199.90 mm (nominal) ID PP tubes with 10.0 mm nominal wall thickness
202.3 mm (nominal) OD PP flow distributor
Polymethacrylate based HIC chromatography media
Instron®-force feedback generating piston
20 ton hydraulic press
Wedgewood conductivity meter
USB data acquisition module (to plot conductivity vs. time trace)

Methods

The column was packed according to sequence discussed herein with reference to FIG. 8. The continuous axial forces required to force the second flow distributor into the tube after the packing medium was packed into the tube were measured and recorded. Also, a column packing efficiency evaluation was conducted after fixing a location of the second flow distributor by detecting pulse injections of NaCl as they were flushed through the length of the packed column bed.

Results

Figure 16:
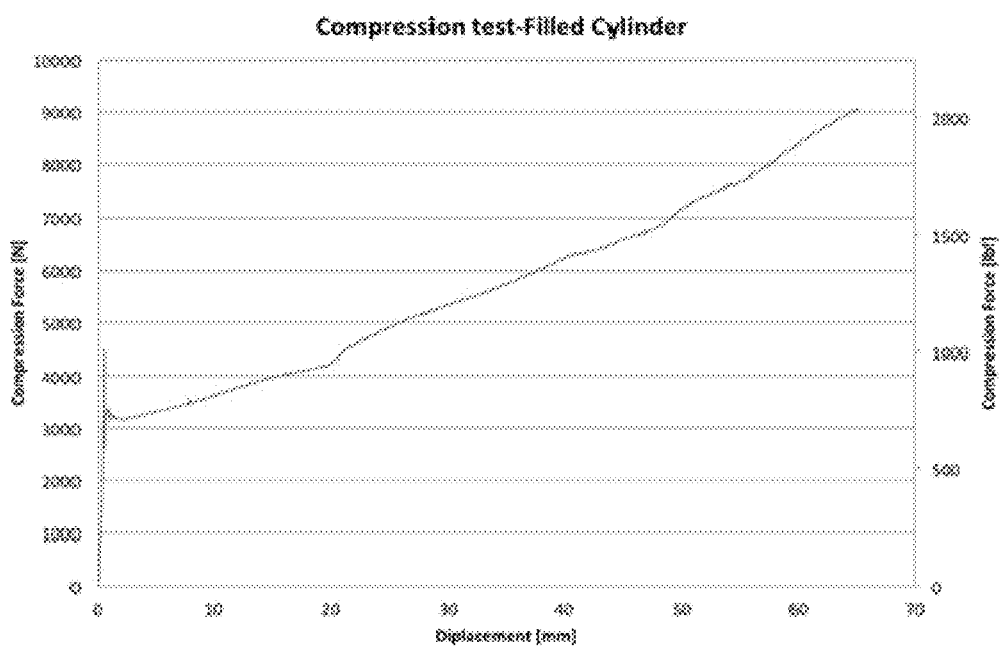
FIG. 16 is plot of observed axial forces needed to press the flow distributor into a tube packed with medium material.
Figure 17:
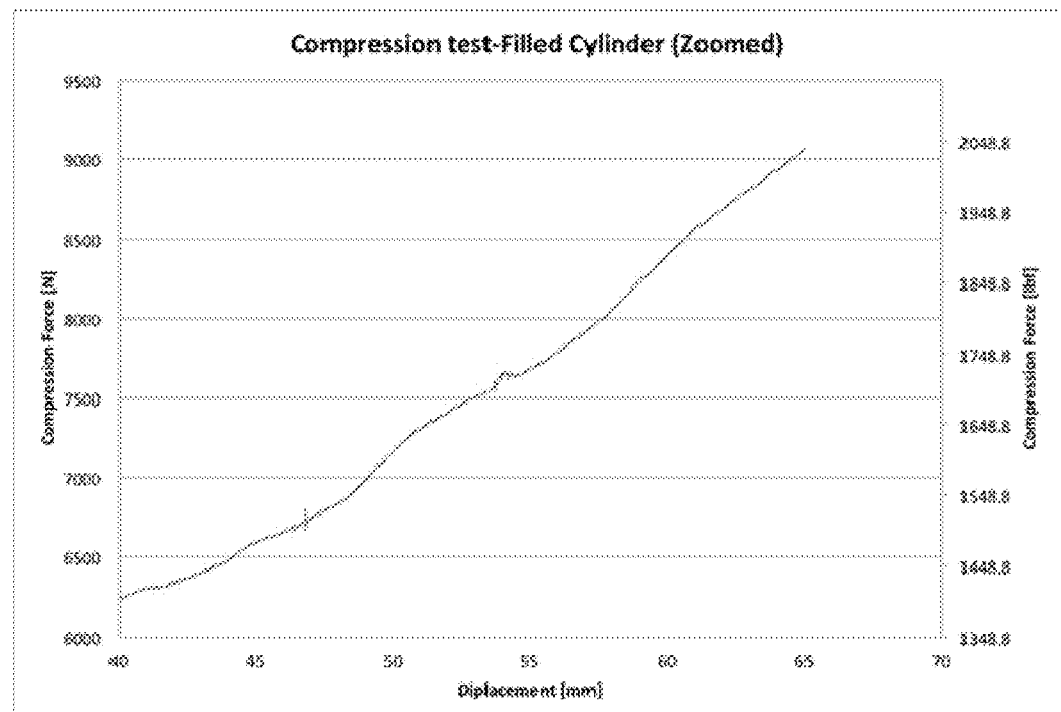
FIG. 17 is an enlarged plot of the data illustrated in FIG. 16.

FIG. 16 is a plot of observed axial forces needed to press the flow distributor into the packed tube. FIG. 17 zooms in on the displacement from 40-70 mm inside the tube from FIG. 16. Two important conclusions can be drawn from FIGS. 16 and 17:

1. The axial force required to push the flow distributor into the tube increased the further the flow distributor was pushed into the tube. As previously noted and shown in FIGS. 10*a* and 10*b*, this is due to the increased hoop tension (and associated stresses) experienced around the flow distributor walls and 3-5 characteristic dimensions above and below the flow distributor in the column wall.

2. The flow distributor and tube wall experienced 2.4 mm of diametrical interference, thus relating to approximately 70 PSI of attainable inner operating pressure without leaking as explained in Example 2. Further checking the validity of Example 2, one can see that the Induced Hoop Tension corresponding to 70 PSI of Leak Pressure also relates to an Axial Force of approximately 4000 N. Looking at FIG. 16, the flow distributor required approximately 4500 N of axial force to travel into the tube. Of course this value increased as it pressed further into the tube due to the auxiliary induced stresses 3-5 characteristic dimensions before and after the point of contact between the flow distributor and tube.

Figure 18:
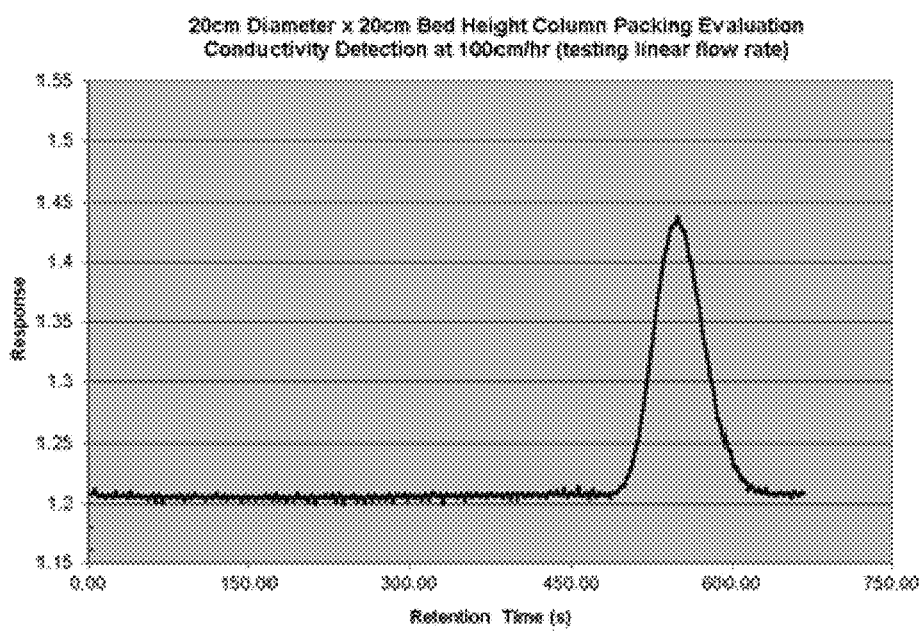
FIG. 18 is a chromatogram plot of a 100 cm/hr packing evaluation.

FIG. 18 is a chromatogram plot of a 100 cm/hr packing evaluation performed on the packed tube.

Table 3 summarizes the data obtained from the column packing study.

TABLE 3

| Test Linear Flow Rate (cm/hr) | N/m | Asymmetry Factor ($A_s$) |
|---|---|---|
| 100 | 3820 | 1.27 |
| 180 | 2889 | 1.11 |
| 300 | 1980 | 1.08 |

Conclusion

The data collected reinforces that the induced hoop tension as a result of the interference fit connection methods described herein provide suitable performance characteristics for packing high performing chromatography columns. The observed axial forces required for packing do not exceed forces that can be generated using conventional methods and coincide with the functional requirements as set forth by the media manufacturer.

Example 4—Qualified Cleaning and Sanitization of Polypropylene Columns

Cleanability and sanitization of a 20 cm internal diameter (ID) polypropylene column was assessed for small molecules, endotoxins, and bacteria.

Materials
Cleanability: Assessment of Small Molecule Clearance in a Pre-Packed Polypropylene Column
1. Inorganic phosphate
2. 20 cm×20 cm polypropylene column packed with Sepharose® 6FF
3. 1M sodium phosphate
4. Deionized water
5. Materials necessary for a sensitive colorimetric method was performed capable of detecting phosphate to µM levels Removal of Endotoxin and Bioburden from a Pre-Packed Polypropylene Column
1. 20 cm×20 cm polypropylene column packed with Sepharose® 6FF
2. *E. coli* bacteria at a concentration of 0.5 OD (optical density)
3. Reverse osmosis deionized (RODI)
4. 1 M sodium hydroxide 0.2 µm filter unit
5. 0.1% peptone water
6. Tryptic Soy Agar (TSA) plate
7. Incubator
8. Materials necessary for a gel-clotting limulus amebocyte lysate (LAL) test with a sensitivity of 0.25 EU/mL Methods
1. Cleanability: Assessment of Small Molecule Clearance in a Pre-Packed Polypropylene Column Inorganic phosphate was used as a small molecule tracer. A 20×20 cm polypropylene column packed with Sepharose® 6FF was loaded with 1 column volume of 1M sodium phosphate at a flow rate of 100 cm/h. The phosphate was re-circulated for a total of 4.5 column volumes to ensure saturation. The column was then washed with deionized water for 10 column volumes to remove any traces of phosphate. Samples were collected during load, recirculation, and wash, and then assayed for phosphate. A sensitive colorimetric method was performed capable of detecting phosphate to µM levels. This method is known in the art and for additional details, please refer to Chen P S, Toribara T Y, Warner H (1956). Microdetermination of phosphorus. Anal Chem 28: 1756-1758, which is incorporated herein by reference in its entirety.

2. Removal of Endotoxin and Bioburden from a Pre-Packed Polypropylene Column

A quantitative cleaning investigation was performed to demonstrate the effectiveness of sanitization using sodium hydroxide as a cleaning agent.

Sanitization Procedure:
Flush with 1 M sodium hydroxide in up-flow at 100 cm/h for 30 minutes
Flush with 1 M sodium hydroxide in down-flow at 100 cm/h for 30 minutes
Recirculation of 1 M sodium hydroxide for 2 hours in up-flow at 100 cm/h
Incubation of the column in 1 M sodium hydroxide for 1 hour (static sanitization for compete removal of endotoxins)
Flush with RODI water at 100 cm/h until neutral pH is achieved Samples of pre and post inoculation and sanitization were collected and assayed for microbial colony forming units (CFU) and endotoxin.

Microbial testing was performed by filtering 1 mL of the sample through a 0.2 µm filter unit, washing the filter with 100 mL of 0.1% peptone water, removing the filter from the unit, and placing it on a Tryptic Soy Agar (TSA) plate. The flow-through after the overnight incubation was diluted 1:$10^6$ prior to filtration, while the post-sanitization water rinse was filtered without dilution. The TSA plate was placed in an incubator at 32° C. for 4 days, and colonies are counted at day 2 and day 4.

Figure 19:
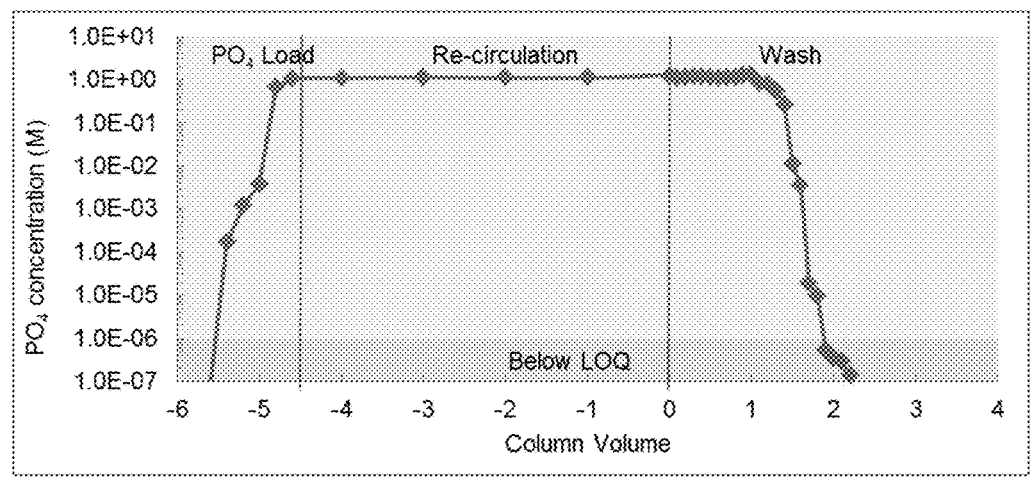
FIG. 19 is a plot illustrating small molecule removal from a column.

Endotoxin testing was performed using gel-clotting limulus amebocyte lysate (LAL) test with a sensitivity of 0.25 EU/mL Results
1. Cleanability: Assessment of Small Molecule Clearance in a Pre-Packed Polypropylene Column FIG. 19 is a graph that demonstrates that a small molecule can easily be removed from a polypropylene column as a result of the well-engineered column design and packing procedures. A reduction of 6 logs is achieved in less than 2 column volumes of wash, and undetectable levels of phosphate are achieved in less than 2.5 column volumes.

2. Removal of Endotoxin and Bioburden from a Pre-Packed Polypropylene Column

Results for bioburden and endotoxin levels from the microbial challenge are outlined in Table 4, which shows the sanitization procedure completely removed bioburden from millions of CFU to zero CFU in the post-sanitization water rinse. In addition, endotoxin levels were brought below the limit of detection (0.25 EU/mL) for the assay.

TABLE 4

| Sample | CFU/mL @ 2 days | CFU/mL @ 4 days | Endotoxin (EU/mL) |
| --- | --- | --- | --- |
| Pre-inoculation water rinse | 0 | 0 | <0.25 |
| Flow-through overnight incubation | 9 × $10^6$ | 9 × $10^6$ | >0.25 |
| Post-sanitization water rinse | 0 | 0 | <0.25 |

Conclusions

Through the phosphate removal experiments, the innovative design of the columns described herein has been qualified for cleaning applications required in downstream processing. The results of the cleaning experiments demonstrate the absence of significant dead-spaces in the column design and the ease of cleaning a pre-packed polypropylene column. Such columns are therefore suitable for use in standard downstream processing applications and can withstand the cleaning protocols required in today's downstream processing applications.

To test effectiveness of sanitization on a polypropylene column made in accordance with the present description, a worst case scenario was devised where the column was loaded with an excess of *E. coli* culture (a gram-negative, endotoxin producing bacteria). The results of the sanitization protocol demonstrate the effective removal of bioburden and endotoxin contamination.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, embodiments, and modifications are within the scope of the following claims.

What is claimed is:
1. A method of making and loading a chromatography column, the method comprising:
   selecting a column tube that has an inner surface having an inner diameter and a length to accommodate a volume of packing medium, the column tube having an elasticity and a wall thickness;

selecting first and second flow distributors each having an outer circumferential surface having an outer diameter;

permanently securing the first flow distributor to a first end of the column tube;

loading the packing medium into the column tube;

inserting the entire second flow distributor into a second end of the column tube, wherein the outer diameter of the second flow distributor is larger than the inner diameter of the column tube before the second flow distributor is inserted into the second end of the column tube, by applying an axial force sufficient to drive the second flow distributor into the column tube, expand the inner diameter of the column tube, and establish an interference fit between the outer circumferential surface of the second flow distributor and the inner surface of the column tube to form a sealed chamber within the column tube between the first and second flow distributors, wherein the interference fit enables the chromatography column to withstand operational pressures and maintain a hydraulic seal without the second flow distributor being permanently secured in position;

after inserting the second flow distributor and establishing the interference fit, adjusting a longitudinal position of the second flow distributor within the column tube by (i) applying an additional axial force to move the second flow distributor further into the column tube, or (ii) forcing liquid into the sealed chamber to apply a hydraulic force to move the second flow distributor back towards the second end of the column tube, or any combination of (i) and (ii); and when the second flow distributor has reached a final longitudinal position, permanently securing the second flow distributor within the column tube at the final longitudinal position.

2. The method of claim 1, wherein the column tube comprises plastic.

3. The method of claim 1, wherein the second flow distributor is permanently secured by welding.

4. The method of claim 1, wherein the outer diameter of the second flow distributor is about 0.25% to 5% larger than the inner diameter of the column tube before the second flow distributor is inserted into the second end of the column tube.

5. The method of claim 1, wherein as a result of the interference fit no gap is formed between the outer circumferential surface of the second flow distributor and the inner surface of the column tube.

6. The method of claim 1, wherein the outer diameter of the first flow distributor is larger than the inner diameter of the column tube before the first flow distributor is inserted into the column tube, and wherein securing the first flow distributor to the first end of the column tube comprises inserting the entire first flow distributor into the first end of the column tube by applying an axial force sufficient to drive the first flow distributor into the column tube to establish an interference fit between the outer circumferential surface of the first flow distributor and the inner surface of the column tube.

7. The method of claim 1, wherein the axial force to drive the second flow distributor into the column tube to establish the interference fit within the column tube is about 1000 lbf to about 10000 lbf.

8. The method of claim 1, wherein the first flow distributor is formed as an integral component of the column tube.

9. The method of claim 1, wherein the interference fit provides a seal to prevent leakage of the packing medium.

10. The method of claim 1, wherein the wall thickness of at least the second end of the column tube is gradually reduced from a full wall thickness to form a chamfer that is thinnest at the second end of the column tube.

11. A method of making and loading a chromatography column, the method comprising:

selecting a column tube that has an inner surface having a diameter and length to accommodate a volume of packing medium, the column tube having an elasticity and a wall thickness;

selecting first and second flow distributors each having an outer circumferential surface having an outer diameter;

permanently securing the first flow distributor to a first end of the column tube;

loading the packing medium into the column tube;

inserting the entire second flow distributor into a second end of the column tube, wherein the outer diameter of the second flow distributor is larger than the inner diameter of the column tube before the second flow distributor is inserted into the second end of the column tube, by applying an axial force sufficient to drive the second flow distributor into the column tube, expand the inner diameter of the column tube, and establish an initial interference fit between the outer circumferential surface of the second flow distributor and the inner surface of the column tube at an initial longitudinal position to provide an initial seal to prevent leakage of the packing medium without the second flow distributor being permanently secured at the initial longitudinal position, wherein the initial interference fit enables the chromatography column to withstand operational pressures and maintain a hydraulic seal without the second flow distributor being permanently secured in position;

after inserting the second flow distributor, testing a performance characteristic of the loaded chromatography column;

determining that the performance characteristic suggests adjustment of the initial longitudinal position to a final longitudinal position, and adjusting the initial longitudinal position of the second flow distributor within the column tube by (i) applying an additional axial force to move the second flow distributor further into the column tube, or (ii) forcing liquid into the chamber to apply a hydraulic force to move the second flow distributor back towards the second end of the column tube, or any combination of (i) and (ii); and when the second flow distributor has been moved to the final longitudinal position, permanently securing the second flow distributor within the column tube at the final longitudinal position.

12. The method of claim 11, wherein the initial longitudinal position of the second flow distributor is different from the final longitudinal position.

13. The method of claim 11, further comprising retesting the performance characteristic of the chromatography column after the second flow distributor is permanently secured within the column tube.

14. The method of claim 11, further comprising retesting the performance characteristic of the chromatography column after adjusting the longitudinal position of the second flow distributor within the column tube.

15. The method of claim 11, wherein the second flow distributor is permanently secured when the performance characteristic of the chromatography column meets a specified level.

16. The method of claim 11, wherein testing the performance characteristic of the chromatography column includes (i) a Height Equivalent to a Theoretical Plate test, (ii) an asymmetry analysis test, or (iii) any combination of (i) and (ii).

17. The method of claim 11, wherein the wall thickness of at least the second end of the column tube is gradually reduced from a full wall thickness to form a chamfer that is thinnest at the second end of the column tube.

* * * * *

UNITED STATES PATENT AND TRADEMARK OFFICE
CERTIFICATE OF CORRECTION

PATENT NO. : 10,188,964 B2
APPLICATION NO. : 13/754540
DATED : January 29, 2019
INVENTOR(S) : Daniel P. Witt et al.

It is certified that error appears in the above-identified patent and that said Letters Patent is hereby corrected as shown below:

In the Specification

Column 15, Line 10, replace "where $F_{radical}$ is" with -- where $F_{radial}$ is --.

Signed and Sealed this
First Day of October, 2019

Andrei Iancu
*Director of the United States Patent and Trademark Office*